United States Patent
Zhou et al.

(10) Patent No.: US 9,847,220 B2
(45) Date of Patent: Dec. 19, 2017

(54) AZIDE-BASED CROSSLINKING AGENTS

(71) Applicant: BASF SE, Ludwigshafen (DE)

(72) Inventors: Mi Zhou, Singapore (SG); Fulvio G. Brunetti, Singapore (SG); Emmanuel Martin, Folgensbourg (FR); Stefan Becker, Ludwigshafen (DE); Iori Doi, Singapore (SG); Raissa Nathania Santoso, Singapore (SG); Mei Shan Lam, Singapore (SG)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/903,138

(22) PCT Filed: Jun. 30, 2014

(86) PCT No.: PCT/IB2014/062720
§ 371 (c)(1),
(2) Date: Jan. 6, 2016

(87) PCT Pub. No.: WO2015/004563
PCT Pub. Date: Jan. 15, 2015

(65) Prior Publication Data
US 2016/0155633 A1 Jun. 2, 2016

(30) Foreign Application Priority Data

Jul. 8, 2013 (EP) .................... 13175494

(51) Int. Cl.

| | |
|---|---|
| H01L 21/02 | (2006.01) |
| C07D 333/20 | (2006.01) |
| C07D 333/22 | (2006.01) |
| C07C 247/16 | (2006.01) |
| H01L 51/00 | (2006.01) |
| H01L 51/05 | (2006.01) |
| C08J 3/24 | (2006.01) |
| C08J 3/28 | (2006.01) |
| C08K 5/28 | (2006.01) |
| C08K 5/45 | (2006.01) |
| C09D 125/06 | (2006.01) |

(52) U.S. Cl.
CPC ...... *H01L 21/02118* (2013.01); *C07C 247/16* (2013.01); *C07D 333/20* (2013.01); *C07D 333/22* (2013.01); *C08J 3/24* (2013.01); *C08J 3/28* (2013.01); *C08K 5/28* (2013.01); *C08K 5/45* (2013.01); *C09D 125/06* (2013.01); *H01L 51/0018* (2013.01); *H01L 51/052* (2013.01); *C07C 2603/18* (2017.05); *C08J 2325/06* (2013.01); *H01L 51/0541* (2013.01); *H01L 51/0545* (2013.01)

(58) Field of Classification Search
CPC .................................. H01L 21/02118
USPC ...................................... 549/70
See application file for complete search history.

(56) References Cited

U.S. PATENT DOCUMENTS

| | | |
|---|---|---|
| 6,451,459 B1 | 9/2002 | Tieke et al. |
| 8,629,238 B2 | 1/2014 | Dueggeli et al. |
| 8,796,469 B2 | 8/2014 | Hayoz et al. |
| 8,835,579 B2 | 9/2014 | Lamatsch et al. |
| 8,912,305 B2 | 12/2014 | Duggeli et al. |
| 8,975,359 B2 | 3/2015 | Duggeli et al. |
| 9,067,942 B2 | 6/2015 | Hayoz et al. |
| 2012/0244294 A1 | 9/2012 | Ho et al. |
| 2015/0029638 A1 | 1/2015 | Kirner et al. |

FOREIGN PATENT DOCUMENTS

| | | |
|---|---|---|
| WO | WO-2004100282 A2 | 11/2004 |
| WO | WO-2005/049695 A1 | 6/2005 |
| WO | WO-2005/052027 A1 | 6/2005 |
| WO | WO-2007/004995 A1 | 1/2007 |
| WO | WO-2008/000664 A1 | 1/2008 |
| WO | WO-2009/068884 A1 | 6/2009 |
| WO | WO-2010/049321 A1 | 5/2010 |
| WO | WO-2010/049323 A1 | 5/2010 |
| WO | WO-2010/108873 A1 | 9/2010 |

(Continued)

OTHER PUBLICATIONS

International Search Report for PCT/I62014/062720 dated Nov. 25, 2014.

(Continued)

*Primary Examiner* — Taofiq A Solola
(74) *Attorney, Agent, or Firm* — Drinker Biddle & Reath LLP

(57) ABSTRACT

The present invention provides compounds of formula

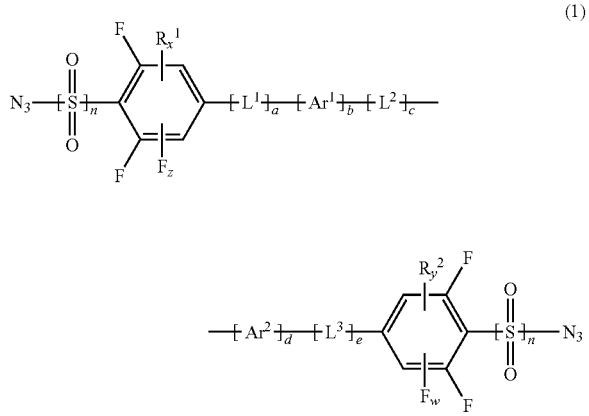

a process for their preparation, a solution comprising these compounds, a process for the preparation of a device using the solution, devices obtainable by the process and the use of the bis-azide-type compounds as cross-linkers.

17 Claims, 6 Drawing Sheets

(56) References Cited

FOREIGN PATENT DOCUMENTS

| WO | WO-2010/115767 A1 | 10/2010 |
| WO | WO-2010/136352 A1 | 12/2010 |
| WO | WO-2010/136353 A1 | 12/2010 |
| WO | WO-2011068482 A1 | 6/2011 |
| WO | WO-2012/059386 A1 | 5/2012 |
| WO | WO-2013/144856 A1 | 10/2013 |

OTHER PUBLICATIONS

Yan, M., et al., "Evaluation of bis (perfluotrophenyl azide) as cross-linkers for a soluble polyimide", J. Mater Chem., 1996, vol. 6, No. 8, pp. 1249-1252.

AZIDE-BASED CROSSLINKING AGENTS

CROSS-REFERENCE TO RELATED APPLICATIONS

This application is a national stage application (under 35 U.S.C. §371) of PCT/IB2014/062720, filed Jun. 30, 2014, which claims benefit of European Application No. 13175494.7, filed Jul. 8, 2013, both applications of which are incorporated herein by reference in their entirety.

The present invention relates bis-azide-type compounds, to a process for their preparation, to a solution comprising these compounds, to a process for the preparation of a device using this solution, to devices obtainable by this process and to the use of the bis-azide-type compounds as cross-linkers.

BACKGROUND OF THE INVENTION

The preparation of electronic devices such as field effect transistor (FET) devices, light emitting devices (LED) and photovoltaic (PV) devices usually comprises the application and structuring, also called patterning, of various layers such as the application and structuring of the electrodes, as well as, the application and structuring of the semiconducting layer, the dielectric layer and of other layers such as barrier layers.

The electrode material is usually applied by evaporation followed by structuring of the electrode material layer using photolithography, which involves the application of a photoresist-layer, exposure of the photoresist-layer to radiation using a mask, removal of the photo-resist not-exposed to radiation, etching of the exposed electrode material, and removal of the remaining photo-resist.

The most convenient way to apply the semiconducting layer, the dielectric layer and other layers such as barrier layers is by solution processing techniques such as spin coating or printing. When using liquid processing techniques it is important that the solution of the layer to be applied does not dissolve the layer already present in the device. Thus, one needs to either use solvents that do not dissolve the layer already present, so-called orthogonal solvents, or render the layer already present in the device insoluble or less soluble towards the solvent of the next layer to be applied. One way to render a polymer layer insoluble or less soluble towards the solvent of the next layer to be applied is by cross-linking this polymer layer. Depending on the cross-linkers used, the crosslinking can be initiated by thermal treatment or by radiation treatment. Radiation treatment has the advantage compared to thermal treatment that by using a mask only part of the polymer layer are cross-linked so that the cross-linking and the structuring step can be combined in one step. The not cross-linked polymer can be easily removed by washing with a suitable solvent, whereas structuring of a polymer layer cross-linked by thermal treatment is usually performed using photolithography, which involves a serious of steps as outlined above for the application and structuring of the electrodes.

Bis-azide-type compounds are cross-linkers that can be activated by radiation treatment. Several bis-azide-type compounds and their application in the preparation of electronic devices have already been described.

Cai, S. X.; Glenn, D. J.; Kanskar, M.; Wybourne, M. N.; Keana, J. F. W. *Chem. Mater* 1994, 6, 1822-1829 describes the following bis-azide-type compounds

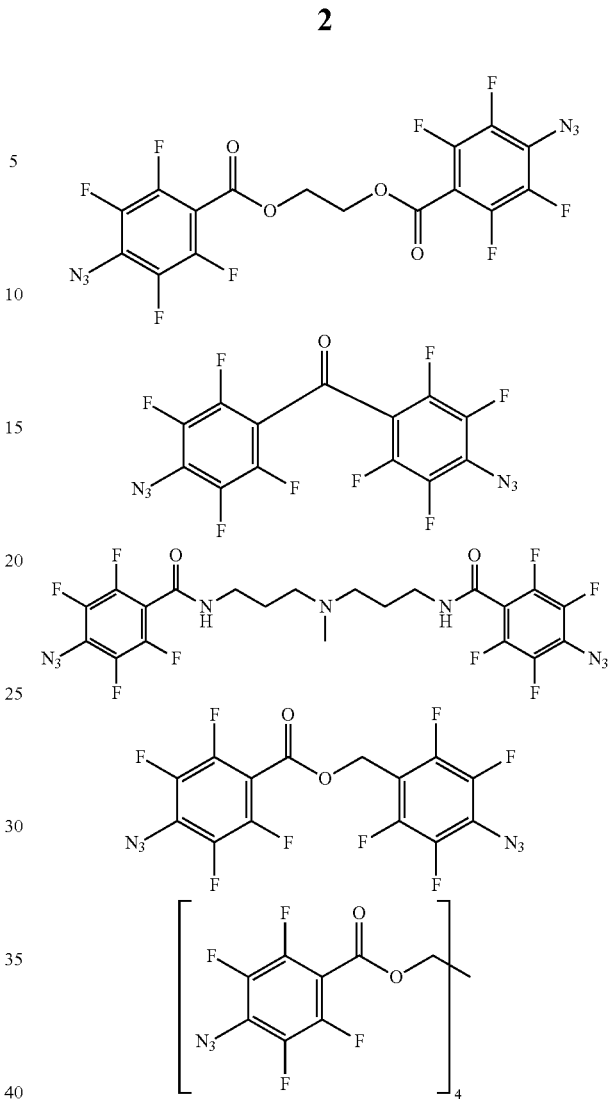

Polystyrene mixtures containing the cross-linkers above were evaluated as deep-UV and electron beam resists.

Yan, M.; Cai, S. X.; Wybourne, M. N.; Keana, J. F. W. *J. Mater. Chem.* 1996, 6, 1249-1252 describes the following bis-azide-type compounds

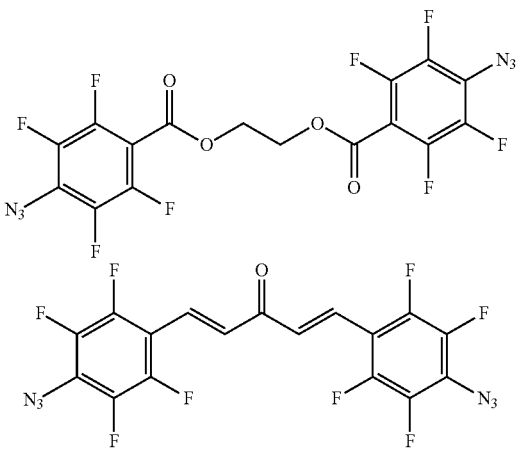

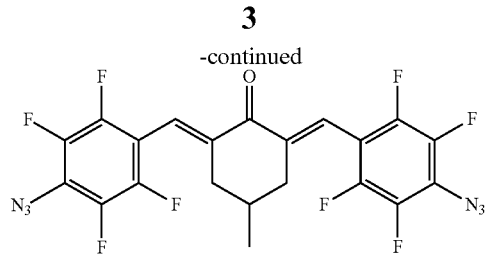

Polyimide mixtures containing the cross-linkers above were evaluated as negative resists.

Touwslager, F. J.; Willard, N. P.; Leeuw, D. M. *Applied Physics Letters* 2002, 81, 4556 describes a lithography process for forming a layer from poly(3,4-ethylenedioxythiophene) (PEDOT). The fully water-borne process is based on photocross-linking PEDOT using the following bis-azide-type compound

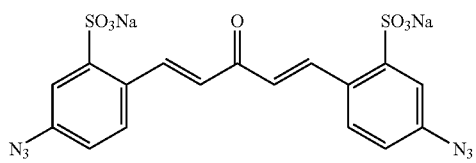

The technology has been applied to fabricate an all-polymer field-effect transistor and integrated circuit.

WO 04/100282 describes a method of forming a polymer device including the steps of (i) depositing on a substrate a solution comprising a polymer or oligomer and a crosslinking moiety to form a layer, (ii) curing the layer formed in step (i) under conditions to form an insoluble cross-linked polymer, characterized in that the crosslinking moiety is present in step (i) in an amount in the range of 0.05 to 5 mol % based on the total number of moles of repeat units of the polymer or oligomer and the crosslinking moiety in the solution. Polymer devices include field-effect transistors. It is preferred that the crosslinking moiety has an absorption in the narrow transmission window in the deep ultraviolet. Typically, this will be in the range 200 to 300 nm. WO 04/100282 exemplifies the following cross-linking moieties:

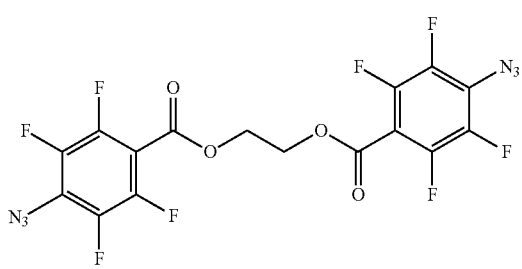

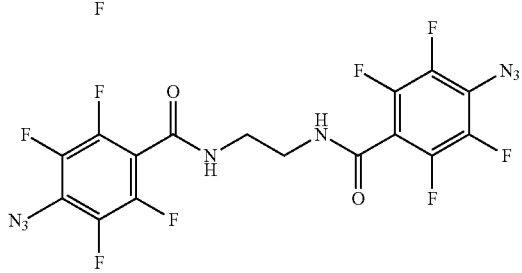

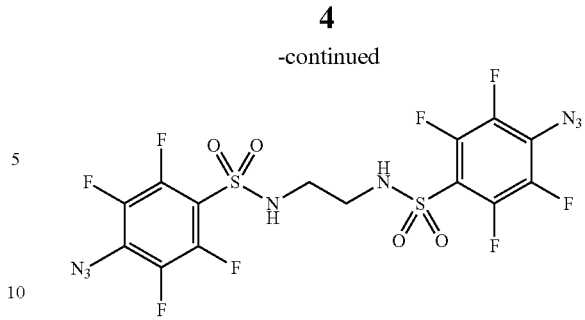

WO 2007/004995 describes a class of cross-linking compound, said compound comprising (i) one or more fluorinated aromatic group and (ii) one or more ionisable group, wherein the cross-linking compound is soluble in at least one polar solvent. The general formula of this class of cross-linking compound is given by formula $N_3$—$Ar_F$-Z (R)—$N_3$ (I), wherein $Ar_F$-Z comprises one or more fluorinated aromatic groups, and R comprises one or more ionisable group, wherein the cross-linking compound is soluble in at least one polar solvent. WO 20071004995 also describes a process of forming a device comprising a polymer is provided, the process includes the steps of (i) depositing a film from a solution comprising a polymer and the crosslinking compound on a substrate and (ii) soft-baking the film at a temperature between 100 to 130° C.; and (iii) exposing the solution in step (ii) to radiation having a wavelength in a range of 250 to 450 nm. Exemplified is the cross-linking compound of formula

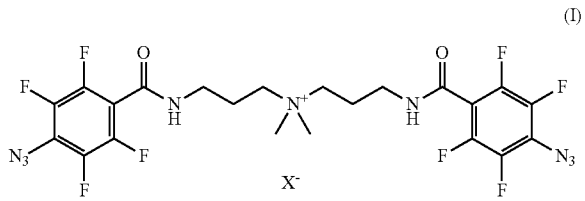

(I)

wherein X is selected from I, $PF_6$, $BF_4$, $ClO_4$ and $CF_3COO$,

WO 2009/068884 describes a supported polymer heterostructure and methods of manufacture. The heterostructure is suitable for use in a range of applications which require semiconductor devices including photovoltaic devices and light-emitting diode devices. For example, a process is described which comprises the steps of preparing a solution of poly(9,9'-dioctylfluorene-co-bis-N,N'-(4-butylphenyl)-bis-N,N-phenyl-1,4-phenylene diamine), polystyrene and the following bis-azide-type photocross-linker

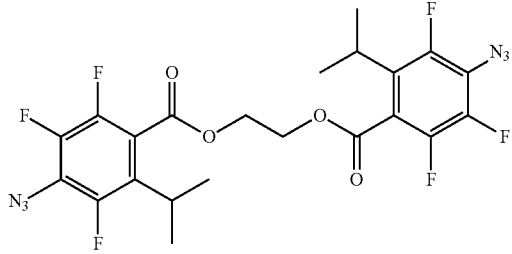 [SMILES: CC(C)c1c(F)c(N=[N+]=[N-])c(F)c(F)c1C(=O)OCCOC(=O)c1c(F)c(F)c(N=[N+]=[N-])c(F)c1C(C)C]

in toluene, spincoating this solution on a support, removing polystyrene by methyl ethyl ketone treatment, and exposing the remaining sample to UV light (254 nm).

Png, R.-Q.; Chia, P.-J.; Tang, J.-C.; Liu, B.; Sivaramakrishnan S.; Zhou, M.; Khong, S.-H.; Chan, H. S. O.; Burroughes, J. H.; Chua, L.-L.; Friend, R. H.; Ho, P. K. H. *Nature Materials* 2010, 9(2), 152-152 describes that sterically hindered bis(fluorophenyl azides) can be mixed generally into polymer organic semiconductors to cause photo-cross-linking when exposed to deep-ultraviolet light (254 nm wavelength). An example of a sterically hindered bi(fluorophenyl azide is

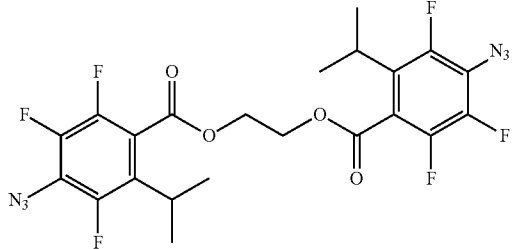 [SMILES: CC(C)c1c(F)c(N=[N+]=[N-])c(F)c(F)c1C(=O)OCCOC(=O)c1c(F)c(F)c(N=[N+]=[N-])c(F)c1C(C)C]

For example, a preparation of an OFET is described which comprises the step of photocross-linking poly 2,5-bis(3-tetradecylthiophene-2-yl)thieno[3,2-b]thiophene) films on an octadecyltrichlorosilylated thermal oxide gate dielectric with $p^{++}$-Si back gate and lithographically patterned AU source-drain electrodes.

WO 2011/068482 describes the cross-linking moiety having a general formula $N_3$—$Ar_F$—W (I), wherein $Ar_F$ comprises a fluorinated phenyl azide group having at least one non-fluorine substituent that is bulkier than fluorine at a meta position relative to the azide group, and W comprises an electron withdrawing group. WO 2011/068482 also describes a solution comprising the cross-linking moiety, and optionally a polymer or oligomer. WO 2011/068482 also describes a method for forming a polymer device comprising the steps of (a) depositing a solution comprising a polymer or oligomer and a cross-linking moiety on a substrate to form a layer, and (b) curing the layer to form an insoluble cross-linked polymer. The device may be a polymer FET device. For example, example 3 of WO 2011/068482 describes the following cross-linking moiety

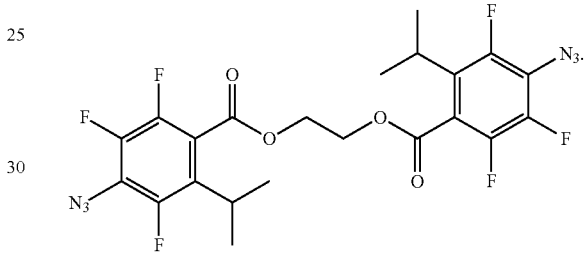

The bis-azide-type compounds described in the literature citations above usually absorb at a wavelength of 254 nm.

DETAILED DESCRIPTION OF THE INVENTION

However, in the preparation of electronic devices, the photoresist-layer used when structuring the electrode material layer or other layers is usually exposed to a wavelength in the range of 300 to 450 nm, in particular to wavelengths of 365 nm, 405 nm or 436 nm, which correspond to the so-called i-line (365 nm), h-line (405 nm) and g-line (436 nm) of a Hg lamp. Thus, it would be very convenient to have bis-azide-type compounds that also absorb at a wavelength in the range of 300 to 450 nm, preferably have their absorption maximum at or close by a wavelength of 365 nm, 405 nm or 436 nm. This would allow the preparation of devices using the same wavelength for the photoresist-layer and for the crosslinking of the polymer layer, without the need to adjust the wavelength of the photo-device or to even replace the photo-device by a radiation device suitable for cross-linking of the polymer layer during the preparation process.

Thus, it was the object of the present invention to provide bis-azide-type compounds that absorb at a wavelength in the range of 300 to 450 nm, and ideally, but not necessarily, have their absorption maximum near or close by a wavelength usually used in photolithography such as 365 nm, 405 nm or 436 nm.

This object is solved by the compounds of claim 1, the process of claim 8, the solution of claim 9, the process of claim 12, and by the device of claim 15.

The compounds of the present invention are of formula (1)

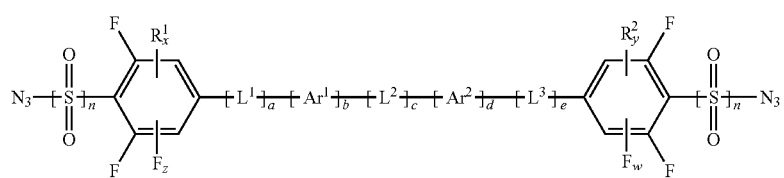

wherein
a is 0, 1 or 2,
b is 1, 2, 3 or 4,
c is 0 or 1,
d is 0, 1, 2, 3 or 4,
e is 0, 1 or 2,
x is 0, 1 or 2,
y is 0, 1 or 2,
z is 0, 1 or 2,
w is 0, 1 or 2,
n is 0 or 1,
$Ar^1$ and $Ar^2$ are independently from each other and at each occurrence an aromatic or heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$,
  wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl,
  wherein $C_{1-20}$-alkyl and $C_{5-8}$-cycloalkyl can be substituted with one or more substituents $R^{aa}$ at each occurrence selected from the group consisting of phenyl, $COOR^{12}$, $CONR^{12}R^{13}$, $COR^{12}$, $SO_3R^{12}$, CN, $NO_2$, halogen, $OR^{12}$, $SR^{12}$, $NR^{11}R^{12}$, $OCOR^{12}$ and $NR^{12}COR^{13}$,
  wherein $C_{6-14}$-aryl and 5 to 12 membered heteroaryl can be substituted with one or more substituent $R^{ab}$ at each occurrence selected from the group consisting of $C_{1-10}$-alkyl, cyclopentyl, cyclohexyl, $COOR^{12}$, $CONR^{12}R^{13}$, $COR^{12}$, $SO_3R^{12}$, CN, $NO_2$, halogen, $OR^{12}$, $SR^{12}$, $NR^{12}R^{13}$, $OCOR^{12}$ and $NR^{12}COR^{13}$,
    wherein $R^{12}$ and $R^{13}$ are independently from each other and at each occurrence $C_{1-10}$-alkyl, cyclopentyl, cyclohexyl or phenyl, and
  wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B,
$L^1$ and $L^3$ are independently from each other and at each occurrence

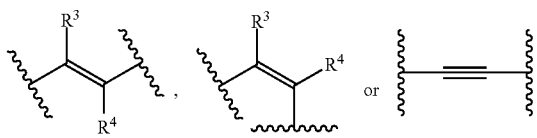

wherein
$R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen,
  wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl,
  wherein $C_{1-20}$-alkyl and $C_{5-8}$-cycloalkyl can be substituted with one or more substituents $R^b$ at each occurrence selected from the group consisting of phenyl, $COOR^{22}$, $CONR^{22}R^{23}$, $COR^{22}$, $SO_3R^{22}$, CN, $NO_2$, halogen, $OR^{22}$, $SR^{22}$, $NR^{22}R^{23}$, $OCOR^{22}$ and $NR^{22}COR^{23}$,
  wherein $C_{6-14}$-aryl and 5 to 12 membered heteroaryl can be substituted with one or more substituent $R^c$ at each occurrence selected from the group consisting of $C_{1-10}$-alkyl, cyclopentyl, cyclohexyl, $COOR^{22}$, $CONR^{22}R^{23}$, $COR^{22}$, $SO_3R^{22}$, CN, $NO_2$, halogen, $OR^{22}$, $SR^{22}$, $NR^{22}R^{23}$, $OCOR^{22}$ and $NR^{22}COR^{23}$,
    wherein $R^{22}$ and $R^{23}$ are independently from each other and at each occurrence $C_{1-10}$-alkyl, cyclopentyl, cyclohexyl or phenyl,
or, if $L^1$ or $L^3$ are

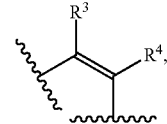

$R^3$ and $R^4$ together with the C-atoms to which they are attached form a 5 to 7-membered non-aromatic ring system A,
$L^2$ is a linking moiety A,
and
$R^1$ and $R^2$ are independently from each other and at each occurrence H, $C_{1-20}$-alkyl, $C_{5-8}$-cycloalkyl, $C_{6-14}$-aryl, 5 to 12 membered heteroaryl, $COOR^{30}$, $CONR^{30}R^{31}$, $COR^{30}$, $SO_3R^{30}$, CN, $NO_2$, halogen, $OR^{30}$, $SR^{30}$, $NR^{30}R^{31}$, $OCOR^{30}$ or $NR^{30}COR^{31}$,
  wherein $R^{30}$ and $R^{31}$ are independently from each other and at each occurrence H, $C_{1-20}$-alkyl, $C_{5-8}$-cycloalkyl, $C_{6-14}$-aryl or 5 to 12 membered heteroaryl,
  wherein $C_{1-20}$-alkyl and $C_{5-8}$-cycloalkyl can be substituted with one or more substituents $R^d$ at each occurrence selected from the group consisting of phenyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$,
  wherein $C_{6-14}$-aryl and 5 to 12 membered heteroaryl can be substituted with one or more substituent $R^e$ at each occurrence selected from the group consisting of $C_{1-10}$-alkyl, cyclopentyl, cyclohexyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$, wherein $R^{32}$ and $R^{33}$ are independently from each other and at each occurrence $C_{1-10}$-alkyl, cyclopentyl, cyclohexyl or phenyl.

Examples of aromatic moieties are $C_{6-14}$-aromatic moieties such as

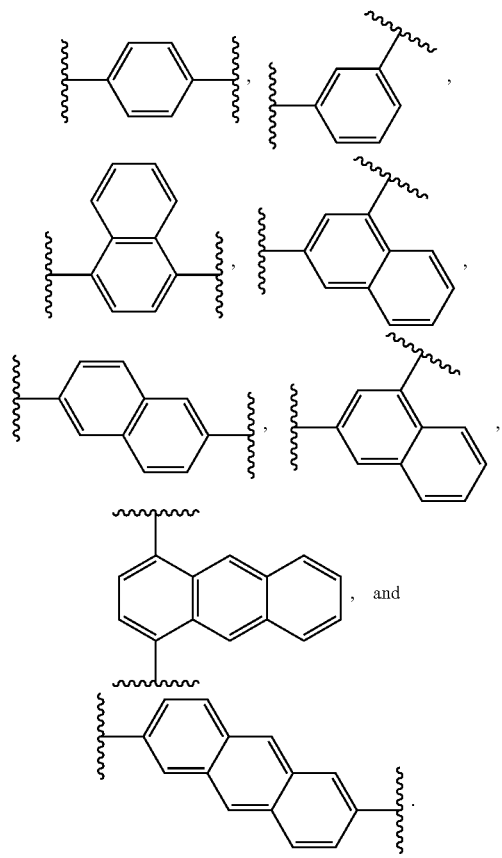

Examples of heteroaromatic moieties are 5 to 14 membered heteroaromatic moieties such as

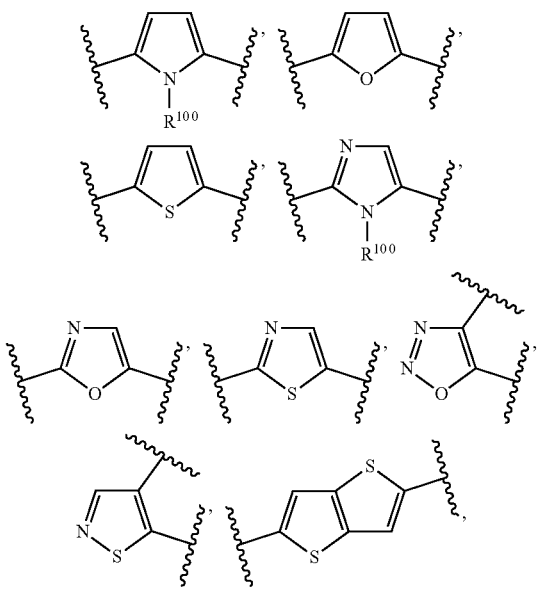

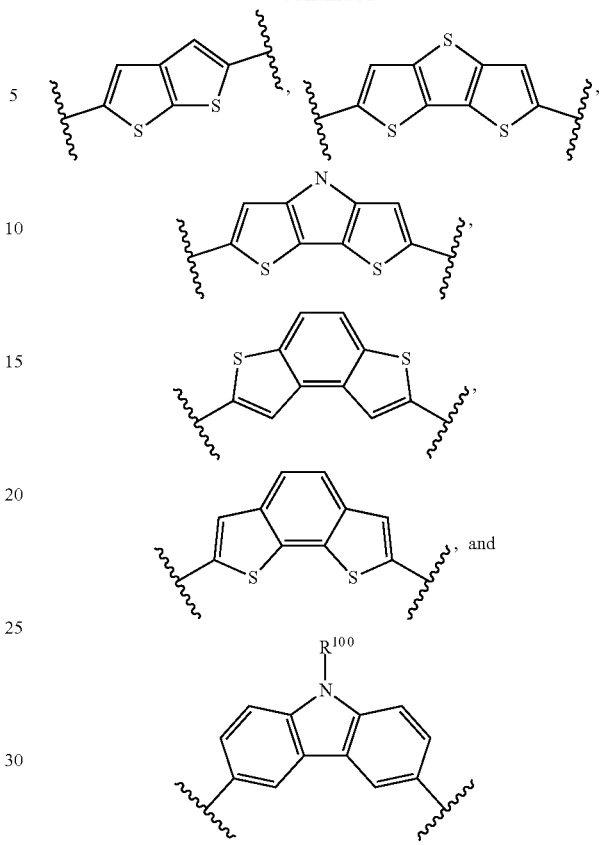

wherein $R^{100}$ is $C_{1-10}$-alkyl.

$C_{1-10}$-alkyl and $C_{1-20}$-alkyl can be branched or unbranched. Examples of $C_{1-10}$-alkyl are methyl, ethyl, butyl, iso-butyl, sec-butyl, tert-butyl, pentyl, isopentyl, hexyl, heptyl, octyl, 1,1-dimethyl-3,3-dimethylbutyl, nonyl and decyl. Examples of $C_{1-20}$-alkyl are $C_{1-10}$-alkyl, undecyl, dodecyl, tridecyl, tetradecyl, pentadecyl, hexadecyl, heptadecyl, octadecyl, nonadecyl and eicosyl. Examples of $C_{3-6}$-alkyl are isopropy, tert-butyl, and isopentyl.

Examples of $C_{5-8}$-cycloalkyl are cyclopentyl, cyclohexyl, cycloheptyl and cyclooctyl.

Examples of $C_{6-14}$-aryl are phenyl and naphthyl.

Examples of 5 to 12 membered heteroaryl are

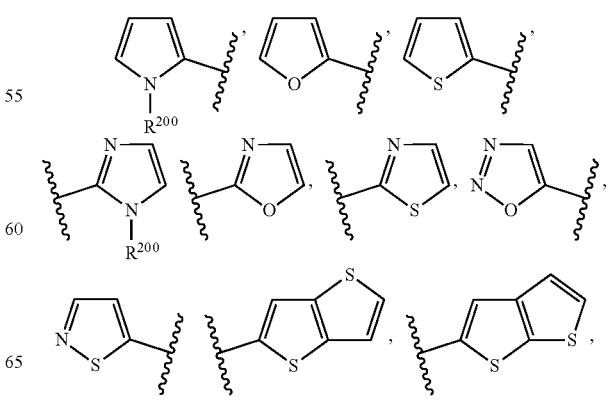

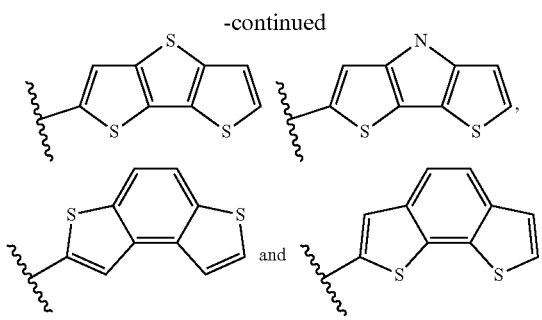

Examples of halogen are F, Cl, Br and I.
Examples of $L^1$ and $L^3$, wherein $L^1$ and $L^3$ are

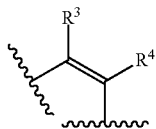

and $R^3$ and $R^4$ together with the C-atoms to which they are attached form a 5 to 7-membered non-aromatic ring system A, are

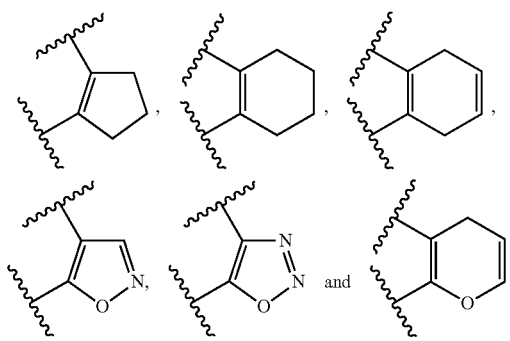

Examples of linking moiety A are $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, which can be substituted with one or more substituent $R^f$ at each occurrence selected from the group consisting of $C_{1-20}$-alkyl, $C_{5-8}$-cycloalkyl, $C_{6-14}$-aryl, 5 to 12 membered heteroaryl, $COOR^{40}$, $CONR^{40}R^{41}$, $COR^{40}$, $SO_3R^{40}$, CN, $NO_2$, halogen, $OR^{40}$, $SR^{40}$, $NR^{40}R^{41}$, $OCOR^{40}$ and $NR^{40}COR^{41}$,
 wherein $R^{40}$ and $R^{41}$ are independently from each other and at each occurrence H, $C_{1-10}$-alkyl, $C_{5-8}$-cycloalkyl, $C_{6-14}$-aryl or 5 to 12 membered heteroaryl,
 wherein $C_{1-20}$-alkyl and $C_{5-8}$-cycloalkyl can be substituted with one or more substituents $R^{fa}$ at each occurrence selected from the group consisting of phenyl, $COOR^{42}$, $CONR^{42}R^{43}$, $COR^{42}$, $SO_3R^{42}$, CN, $NO_2$, halogen, $OR^{42}$, $SR^{42}$, $NR^{42}R^{43}$, $OCOR^{42}$ and $NR^{42}COR^{43}$,
 wherein $C_{6-14}$-aryl and 5 to 12 membered heteroaryl can be substituted with one or more substituent $R^{fb}$ at each occurrence selected from the group consisting of $C_{1-10}$-alkyl, cyclopentyl, cyclohexyl, $COOR^{42}$, $CONR^{42}R^{43}$, $COR^{42}$, $SO_3R^{42}$, CN, $NO_2$, halogen, $OR^{42}$, $SR^{42}$, $NR^{42}R^{43}$, $OCOR^{42}$ and $NR^{42}COR^{43}$,
 wherein $R^{42}$ and $R^{43}$ are independently from each other and at each occurrence $C_{1-10}$-alkyl, cyclopentyl, cyclohexyl or phenyl, and
 wherein one or more $CH_2$ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)$NR^{50}$, $SO_2$—$NR^{50}$, $NR^{50}$, $NR^{50}R^{61}$, O or S,
 wherein $R^{50}$ and $R^{51}$ are independently from each other and at each occurrence $C_{1-10}$-alkyl.

Examples of linking moiety B is $C_{1-4}$-alkylene, which can be substituted with one or more $C_{1-10}$-alkyl, wherein one or more $CH_2$ groups of $C_{1-4}$-alkylene can be replaced by C=O, (C=O)O, (C=O)$NR^{60}$, $SO_2$—$NR^{60}$, $NR^{60}$, $NR^{60}R^{61}$, O or S,
 wherein $R^{60}$ and $R^{61}$ are independently from each other and at each occurrence $C_{1-10}$-alkyl.

Examples of $C_{1-4}$-alkylene are methylene, ethylene, propylene and butylene. Examples of $C_{1-10}$-alkylene are $C_{1-4}$-alkylene as well as pentylene, hexylene, heptylene, octylene, nonylene and decylene.

Examples of $C_{2-4}$-alkenylene are methenylene, ethenylene, propenylene and butenylene. Examples of $C_{2-10}$-alkenylene are $C_{2-4}$-alkenylene as well as pentenylene, hexenylene, heptenylene, octenylene, nonenylene and decenylene.

Examples of $C_{5-8}$-cycloalkylene are cyclopentylene, cyclohexylene, cycloheptylene and cyclooctylene.
Preferably,
 a and e are the same and are 0 or 1,
 b is 1, 2 or 3,
 c is 0 or 1, and
 d is 0, 1, 2 or 3.
More preferably,
 a and e are the same and are 0 or 1,
 b is 1,
 c is 0 or 1, and
 d is 0 or 1.
Preferably,
 x and y are the same and are 0, 1 or 2, and
 z and w are the same and are 0, 1 or 2.
More preferably,
 x and y are the same and are 0 or 1, and
 z and w are the same and are 1 or 2.
Most preferably,
 x and y are the same and are 0,
 z and w are the same and are 2.
Preferably, n is 0.
Preferably, $Ar^1$ and $Ar^2$ are independently from each other and at each occurrence an aromatic or heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$,
 wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl, and
 wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B.

More preferably, $Ar^1$ and $Ar^2$ are independently from each other and at each occurrence a $C_{6-14}$-aromatic or a 5 to 12 membered heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$, wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl, wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B.

Even more preferably, $Ar^1$ and $Ar^2$ are the same and are a $C_{6-14}$-aromatic or a 5 to 12 membered heteroaromatic moiety, which can be substituted with one or more substituent $R^a$ selected from the group consisting of $C_{1-20}$-alkyl and $OR^{10}$, wherein $R^{10}$ is independently from each other and at each occurrence $C_{1-20}$-alkyl, and wherein $Ar^1$ and $Ar^2$, both connected to $L^2$ or if c=0 to each other, can be additionally linked by one or more $L^a$, wherein $L^a$ is a linking moiety B, wherein the linking moiety B is $C_{1-4}$-alkylene, which can be substituted with one or more $C_{1-10}$-alkyl.

Most preferably, $Ar^1$ and $Ar^2$ are the same and are

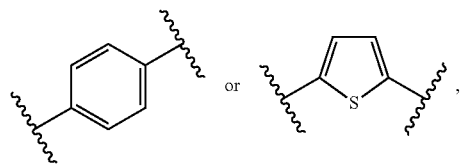 [SMILES: *c1ccc(*)cc1 ; *c1ccc(*)s1]

which can be substituted with one or more substituent $R^a$ selected from the group consisting of $C_{1-10}$-alkyl and $OR^{10}$, wherein $R^{10}$ is independently from each other and at each occurrence $C_{1-10}$-alkyl, and wherein $Ar^1$ and $Ar^2$, both connected to $L^2$ or if c=0 to each other, can be additionally linked by one or more $L^a$, wherein $L^a$ is a linking moiety B, wherein the linking moiety B is methylene substituted with one or more $C_{1-10}$-alkyl.

Preferably, $L^1$ and $L^3$ are independently from each other and at each occurrence

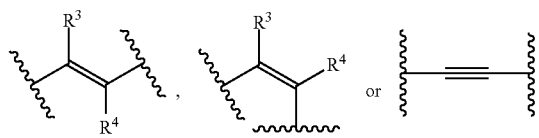

wherein
$R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen,
wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl,
or, if $L^1$ or $L^3$ are

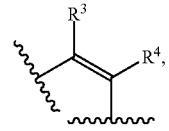

$R^3$ and $R^4$ together with the C-atoms to which they are attached form a 5 to 7-membered non-aromatic ring system A.

More preferably, $L^1$ and $L^3$ are the same and are

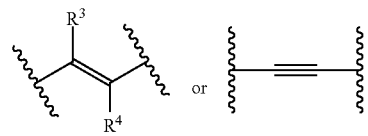

wherein
$R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$ or halogen,
wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl.

Even more preferably, $L^1$ and $L^3$ are the same and are

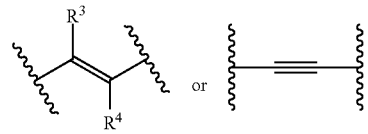

wherein
$R^3$ and $R^4$ are independently from each other and at each occurrence H, $C_{1-20}$-alkyl, $COOR^{20}$, $CONR^{20}R^{21}$, $COR^{20}$, $SO_3R^{20}$, CN, $NO_2$ or halogen,
wherein $R^{20}$ and $R^{21}$ are independently from each other and at each occurrence H or $C_{1-20}$-alkyl.

Most preferably, $L^1$ and $L^3$ are the same and are

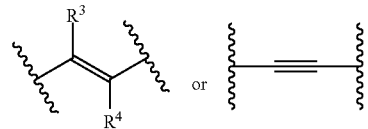

wherein
$R^3$ and $R^4$ are H.

Preferably, $L^2$ is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, which can be substituted with one or more substituent $R^f$ at each occurrence selected from the group consisting of $C_{1-20}$-alkyl, $C_{5-8}$-cycloalkyl, $C_{6-14}$-aryl, 5 to 12 membered heteroaryl, $COOR^{40}$, $CONR^{40}R^{41}$, $COR^{40}$, $SO_3R^{40}$, CN, $NO_2$, halogen, $OR^{40}$, $SR^{40}$, $NR^{40}R^{41}$, $OCOR^{40}$ and $NR^{40}COR^{41}$, wherein R⁴⁰ and R⁴¹ are independently from each other and at each occurrence H, $C_{1-10}$-alkyl, $C_{5-8}$-cycloalkyl, $C_{6-14}$-aryl or 5 to 12 membered heteroaryl, wherein $C_{1-20}$-alkyl and $C_{5-8}$-cycloalkyl can be substituted with one or more substituents $R^{fa}$ at each occurrence selected from the group consisting of phenyl, COOR⁴², CONR⁴²R⁴³, COR⁴², SO₃R⁴², CN, NO₂, halogen, OR⁴², SR⁴², NR⁴²R⁴³, OCOR⁴² and NR⁴²COR⁴³, wherein $C_{6-14}$-aryl and 5 to 12 membered heteroaryl can be substituted with one or more substituent $R^{fb}$ at each occurrence selected from the group consisting of $C_{1-10}$-alkyl, cyclopentyl, cyclohexyl, COOR⁴², CONR⁴²R⁴³, COR⁴², SO₃R⁴², CN, NO₂, halogen, OR⁴², SR⁴², NR⁴²R⁴³, OCOR⁴² and NR⁴²COR⁴³, wherein R⁴² and R⁴³ are independently from each other and at each occurrence $C_{1-10}$-alkyl, cyclopentyl, cyclohexyl or phenyl, and wherein one or more CH₂ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)NR⁵⁰, SO₂—NR⁵⁰, NR⁵⁰, NR⁵⁰R⁵¹, O or S, wherein R⁵⁰ and R⁵¹ are independently from each other and at each occurrence $C_{1-10}$-alkyl.

More preferably, L² is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, which can be substituted with one or more substitutent $R^f$ at each occurrence selected from the group consisting of $C_{1-20}$-alkyl, $C_{5-8}$-cycloalkyl, $C_{6-14}$-aryl, 5 to 12 membered heteroaryl, COOR⁴⁰, CONR⁴⁰R⁴¹, COR⁴⁰, SO₃R⁴⁰, CN, NO₂, halogen, OR⁴⁰, SR⁴⁰, NR⁴⁰R⁴¹, OCOR⁴⁰ and NR⁴⁰COR⁴¹, wherein R⁴⁰ and R⁴¹ are independently from each other and at each occurrence H, $C_{1-10}$-alkyl, $C_{5-8}$-cycloalkyl, $C_{6-14}$-aryl or 5 to 12 membered heteroaryl, and wherein one or more CH₂ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)NR⁵⁰, SO₂—NR⁵⁰, NR⁵⁰, NR⁵⁰R⁵¹, O or S, wherein R⁵⁰ and R⁵¹ are independently from each other and at each occurrence $C_{1-10}$-alkyl.

Even more preferably, L² is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, wherein one or more CH₂ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)NR⁵⁰, SO₂—NR⁵⁰, NR⁵⁰, NR⁵⁰R⁵¹, O or S, wherein R⁵⁰ and R⁵¹ are independently from each other and at each occurrence $C_{1-10}$-alkyl.

Most preferably, L² is a linking moiety A, wherein the linking moiety A is $C_{1-10}$-alkylene, wherein one or more CH₂ groups of $C_{1-10}$-alkylene can be replaced by C=O, (C=O)O, (C=O)NR⁵⁰, SO₂—NR⁵⁰, NR⁵⁰, NR⁵⁰R⁵¹, O or S, wherein R⁵⁰ and R⁵¹ are independently from each other and at each occurrence $C_{1-10}$-alkyl.

Preferably, R¹ and R² are independently from each other and at each occurrence H, $C_{1-20}$-alkyl, $C_{5-8}$-cycloalkyl, $C_{6-14}$-aryl, 5 to 12 membered heteroaryl, COOR³⁰, CONR³⁰R³¹, COR³⁰, SO₃R³⁰, CN, NO₂, halogen, OR³⁰, SR³⁰, NR³⁰R³¹, OCOR³⁰ or NR³⁰COR³¹, wherein R³⁰ and R³¹ are independently from each other and at each occurrence H, $C_{1-20}$-alkyl, $C_{5-8}$-cycloalkyl, $C_{6-14}$-aryl or 5 to 12 membered heteroaryl.

More preferably, R¹ and R² are the same and are H, $C_{1-20}$-alkyl or $C_{5-8}$-cycloalkyl.

Most preferably, R¹ and R² are the same and are branched $C_{3-6}$-alkyl.

In preferred compounds of formula (1) n is 0, and the compounds are of formula

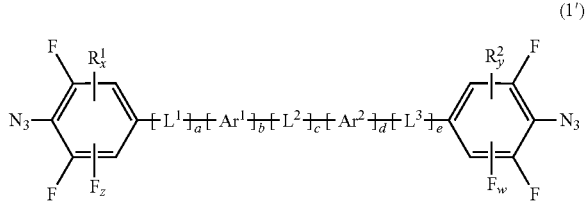

(1')

wherein
a is 0, 1 or 2,
b is 1, 2, 3 or 4,
c is 0 or 1,
d is 0, 1, 2, 3 or 4,
e is 0, 1 or 2,
x is 0, 1 or 2,
y is 0, 1 or 2,
z is 0, 1 or 2,
w is 0, 1 or 2, Ar¹ and Ar² are independently from each other and at each occurrence an aromatic or heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, COOR¹⁰, CONR¹⁰R¹¹, COR¹⁰, SO₃R¹⁰, CN, NO₂, halogen, OR¹⁰, SR¹⁰, NR¹⁰R¹¹, OCOR¹⁰ and NR¹⁰COR¹¹, wherein R¹⁰ and R¹¹ are independently from each other and at each occurrence H, $C_{1-20}$-alkyl, $C_{5-8}$-cycloalkyl, $C_{6-14}$-aryl or 5 to 12 membered heteroaryl, wherein $C_{1-20}$-alkyl and $C_{5-8}$-cycloalkyl can be substituted with one or more substituents $R^{aa}$ at each occurrence selected from the group consisting of phenyl, COOR¹², CONR¹²R¹³, COR¹², SO₃R¹², CN, NO₂, halogen, OR¹², SR¹², NR¹¹R¹², OCOR¹² and NR¹²COR¹³, wherein $C_{6-14}$-aryl and 5 to 12 membered heteroaryl can be substituted with one or more substituent $R^{ab}$ at each occurrence selected from the group consisting of $C_{1-10}$-alkyl, cyclopentyl, cyclohexyl, COOR¹², CONR¹²R¹³, COR¹², SO₃R¹², CN, NO₂, halogen, OR¹², SR¹², NR¹²R¹³, OCOR¹² and NR¹²COR¹³, wherein R¹² and R¹³ are independently from each other and at each occurrence $C_{1-10}$-alkyl, cyclopentyl, cyclohexyl or phenyl, and wherein at least two adjacent Ar¹, at least two adjacent Ar², and/or Ar¹ and Ar², both connected to L² or if c=0 to each other, can be additionally linked by one or more $L^a$, wherein $L^a$ is a linking moiety B, L¹ and L³ are independently from each other and at each occurrence

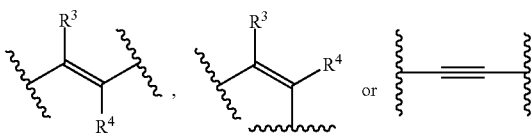

wherein
$R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen,
  wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl,
  wherein $C_{1-20}$-alkyl and $C_{5-8}$-cycloalkyl can be substituted with one or more substituents $R^b$ at each occurrence selected from the group consisting of phenyl, $COOR^{22}$, $CONR^{22}R^{23}$, $COR^{22}$, $SO_3R^{22}$, CN, $NO_2$, halogen, $OR^{22}$, $SR^{22}$, $NR^{22}R^{23}$, $OCOR^{22}$ and $NR^{22}COR^{23}$,
  wherein $C_{6-14}$-aryl and 5 to 12 membered heteroaryl can be substituted with one or more substituent $R^c$ at each occurrence selected from the group consisting of $C_{1-10}$-alkyl, cyclopentyl, cyclohexyl, $COOR^{22}$, $CONR^{22}R^{23}$, $COR^{22}$, $SO_3R^{22}$, CN, $NO_2$, halogen, $OR^{22}$, $SR^{22}$, $NR^{22}R^{23}$, $OCOR^{22}$ and $NR^{22}COR^{23}$,
    wherein $R^{22}$ and $R^{23}$ are independently from each other and at each occurrence $C_{1-10}$-alkyl, cyclopentyl, cyclohexyl or phenyl,
or, if $L^1$ or $L^3$ are

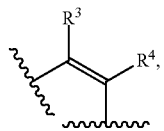

$R^3$ and $R^4$ together with the C-atoms to which they are attached form a 5 to 7-membered non-aromatic ring system A,
$L^2$ is a linking moiety A,
and
$R^1$ and $R^2$ are independently from each other and at each occurrence H, $C_{1-20}$-alkyl, $C_{5-8}$-cycloalkyl, $C_{6-14}$-aryl, 5 to 12 membered heteroaryl, $COOR^{30}$, $CONR^{30}R^{31}$, $COR^{30}$, $SO_3R^{30}$, CN, $NO_2$, halogen, $OR^{30}$, $SR^{30}$, $NR^{30}R^{31}$, $OCOR^{30}$ or $NR^{30}COR^{31}$,
  wherein $R^{30}$ and $R^{31}$ are independently from each other and at each occurrence H, $C_{1-20}$-alkyl, $C_{5-8}$-cycloalkyl, $C_{6-14}$-aryl or 5 to 12 membered heteroaryl,
  wherein $C_{1-20}$-alkyl and $C_{5-8}$-cycloalkyl can be substituted with one or more substituents $R^d$ at each occurrence selected from the group consisting of phenyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$,
  wherein $C_{6-14}$-aryl and 5 to 12 membered heteroaryl can be substituted with one or more substituent $R^e$ at each occurrence selected from the group consisting of $C_{1-10}$-alkyl, cyclopentyl, cyclohexyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$,
    wherein $R^{32}$ and $R^{33}$ are independently from each other and at each occurrence $C_{1-10}$-alkyl, cyclopentyl, cyclohexyl or phenyl.

In more preferred compounds of formula (1) n is 0, and the compounds are of formula (1'), wherein
a is 0, 1 or 2,
b is 1, 2, 3 or 4,
c is 0 or 1,
d is 0, 1, 2, 3 or 4,
e is 0, 1 or 2,
x is 0, 1 or 2,
y is 0, 1 or 2,
z is 0, 1 or 2,
w is 0, 1 or 2,
$Ar^1$ and $Ar^2$ are independently from each other and at each occurrence an aromatic or heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$,
  wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl, and
  wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B,
$L^1$ and $L^3$ are independently from each other and at each occurrence

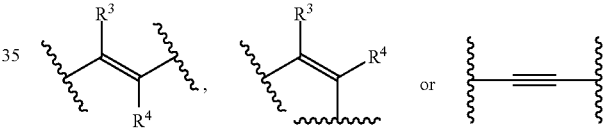

wherein
$R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen,
  wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl,
or, if $L^1$ or $L^3$ are

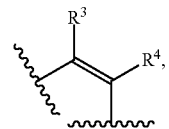

$R^3$ and $R^4$ together with the C-atoms to which they are attached form a 5 to 7-membered non-aromatic ring system A,
$L^2$ is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, which can be substituted with one or more substitutent $R^f$ at each occurrence selected from the group consisting of $C_{1-20}$-alkyl, $C_{5-8}$-cycloalkyl, $C_{6-14}$-aryl, 5 to 12 membered heteroaryl, $COOR^{40}$, $CONR^{40}R^{41}$, $COR^{40}$, $SO_3R^{40}$, CN, $NO_2$, halogen, $OR^{40}$, $SR^{40}$, $NR^{40}R^{41}$, $OCOR^{40}$ and $NR^{40}COR^{41}$, wherein $R^{40}$ and $R^{41}$ are independently from each other and at each occurrence H, $C_{1-10}$-alkyl, $C_{5-8}$-cycloalkyl, $C_{6-14}$-aryl or 5 to 12 membered heteroaryl, wherein $C_{1-20}$-alkyl and $C_{5-8}$-cycloalkyl can be substituted with one or more substituents $R^{fa}$ at each occurrence selected from the group consisting of phenyl, $COOR^{42}$, $CONR^{42}R^{43}$, $COR^{42}$, $SO_3R^{42}$, CN, $NO_2$, halogen, $OR^{42}$, $SR^{42}$, $NR^{42}R^{43}$, $OCOR^{42}$ and $NR^{42}COR^{43}$, wherein $C_{6-14}$-aryl and 5 to 12 membered heteroaryl can be substituted with one or more substituent $R^{fb}$ at each occurrence selected from the group consisting of $C_{1-10}$-alkyl, cyclopentyl, cyclohexyl, $COOR^{42}$, $CONR^{42}R^{43}$, $COR^{42}$, $SO_3R^{42}$, CN, $NO_2$, halogen, $OR^{42}$, $SR^{42}$, $NR^{42}R^{43}$, $OCOR^{42}$ and $NR^{42}COR^{43}$, wherein $R^{42}$ and $R^{43}$ are independently from each other and at each occurrence $C_{1-10}$-alkyl, cyclopentyl, cyclohexyl or phenyl, and wherein one or more $CH_2$ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)$NR^{50}$, $SO_2$—$NR^{50}$, $NR^{50}$, $NR^{50}R^{51}$, O or S, wherein $R^{50}$ and $R^{51}$ are independently from each other and at each occurrence $C_{1-10}$-alkyl, and $R^1$ and $R^2$ are independently from each other and at each occurrence H, $C_{1-20}$-alkyl, $C_{5-8}$-cycloalkyl, $C_{6-14}$-aryl, 5 to 12 membered heteroaryl, $COOR^{30}$, $CONR^{60}R^{31}$, $COR^{30}$, $SO_3R^{30}$, CN, $NO_2$, halogen, $OR^{30}$, $SR^{30}$, $NR^{30}R^{31}$, $OCOR^{30}$ or $NR^{30}COR^{31}$, wherein $R^{30}$ and $R^{31}$ are independently from each other and at each occurrence H, $C_{1-20}$-alkyl, $C_{5-8}$-cycloalkyl, $C_{6-14}$-aryl or 5 to 12 membered heteroaryl.

In even more preferred compounds of formula (1) n is 0, and the compounds are of formula (1'), wherein a and e are the same and are 0 or 1, b is 1, 2 or 3, c is 0 or 1, and d is 0, 1, 2 or 3, x and y are the same and are 0, 1 or 2, and z and w are the same and are 0, 1 or 2, $Ar^1$ and $Ar^2$ are independently from each other and at each occurrence a $C_{6-14}$-aromatic or a 5 to 12 membered heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$, wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl, and wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B, $L^1$ and $L^3$ are the same and are

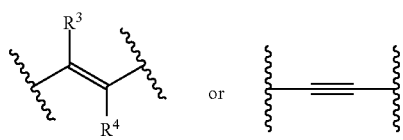

wherein $R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen, wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl, $L^2$ is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, which can be substituted with one or more substituent $R^f$ at each occurrence selected from the group consisting of $C_{1-20}$-alkyl, $C_{5-8}$-cycloalkyl, $C_{6-14}$-aryl, 5 to 12 membered heteroaryl, $COOR^{40}$, $CONR^{40}R^{41}$, $COR^{40}$, $SO_3R^{40}$, CN, $NO_2$, halogen, $OR^{40}$, $SR^{40}$, $NR^{40}R^{41}$, $OCOR^{40}$ and $NR^{40}COR^{41}$, wherein $R^{40}$ and $R^{41}$ are independently from each other and at each occurrence H, $C_{1-10}$-alkyl, $C_{5-8}$-cycloalkyl, $C_{6-14}$-aryl or 5 to 12 membered heteroaryl, and wherein one or more $CH_2$ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)$NR^{50}$, $SO_2$—$NR^{50}$, $NR^{50}$, $NR^{50}R^{51}$, O or S, wherein $R^{50}$ and $R^{51}$ are independently from each other and at each occurrence $C_{1-10}$-alkyl, and $R^1$ and $R^2$ are the same and are H, $C_{1-20}$-alkyl or $C_{5-8}$-cycloalkyl, In most preferred compounds of formula (1) n is 0, and the compounds are of formula (1'), wherein a and e are the same and are 0 or 1, b is 1, c is 0 or 1, and d is 0 or 1, x and y are the same and are 0 or 1, and z and w are the same and are 1 or 2, $Ar^1$ and $Ar^2$ are the same and are a $C_{6-14}$-aromatic or a 5 to 12 membered heteroaromatic moiety, which can be substituted with one or more substituent $R^a$ selected from the group consisting of $C_{1-20}$-alkyl and $OR^{10}$, wherein $R^{10}$ is independently from each other and at each occurrence $C_{1-20}$-alkyl, and wherein $Ar^1$ and $Ar^2$, both connected to $L^2$ or if c=0 to each other, can be additionally linked by one or more $L^a$, wherein $L^E$ is a linking moiety B, wherein the linking moiety B is $C_{1-4}$-alkylene, which can be substituted with one or more $C_{1-10}$-alkyl, $L^1$ and $L^3$ are the same and are

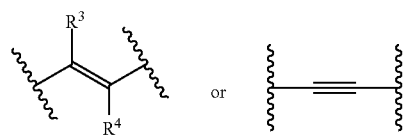

wherein $R^3$ and $R^4$ are independently from each other and at each occurrence H, $C_{1-20}$-alkyl, $COOR^{20}$, $CONR^{20}R^{21}$, $COR^{20}$, $SO_3R^{20}$, CN, $NO_2$ or halogen, wherein $R^{20}$ and $R^{21}$ are independently from each other and at each occurrence H or $C_{1-20}$-alkyl, $L^2$ is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, wherein one or more $CH_2$ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by $C=O$, $(C=O)O$, $(C=O)NR^{50}$, $SO_2-NR^{50}$, $NR^{50}$, $NR^{50}R^{51}$, O or S, wherein $R^{50}$ and $R^{51}$ are independently from each other and at each occurrence $C_{1-10}$-alkyl, and $R^1$ and $R^2$ are the same and are branched $C_{3-6}$-alkyl, In particular preferred compounds of formula (1) n is 0, and the compounds are of formula (1'), wherein a and e are the same and are is 0 or 1, b is 1, c is 0 or 1, and d is 0 or 1, x and y are 0, and z and w are 2, $Ar^1$ and $Ar^2$ are the same and are

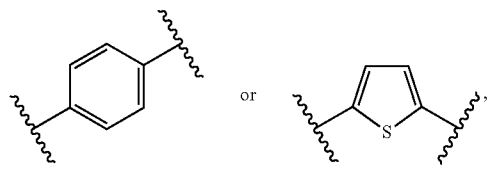 [SMILES: *c1ccc(*)cc1 ; *c1ccc(*)s1]

which can be substituted with one or more substituent $R^a$ selected from the group consisting of $C_{1-10}$-alkyl and $OR^{10}$, wherein $R^{10}$ is independently from each other and at each occurrence $C_{1-10}$-alkyl, and wherein $Ar^1$ and $Ar^2$, both connected to $L^2$ or if c=0 to each other, can be additionally linked by one or more $L^a$, wherein $L^a$ is a linking moiety B, wherein the linking moiety B is methylene substituted with one or more $C_{1-10}$-alkyl, $L^1$ and $L^3$ are the same and are

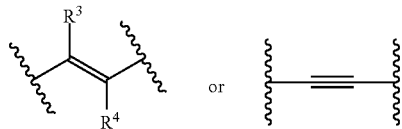

wherein $R^3$ and $R^4$ are H, and $L^2$ is a linking moiety A, wherein the linking moiety A is $C_{1-10}$-alkylene, wherein one or more $CH_2$ groups of $C_{1-10}$-alkylene can be replaced by $C=O$, $(C=O)O$, $(C=O)NR^{50}$, $SO_2-NR^{50}$, $NR^{50}$, $NR^{50}R^{51}$, O or S, $L^2$ is a linking moiety A, wherein the linking moiety A is $C_{1-10}$-alkylene, wherein one or more $CH_2$ groups of $C_{1-10}$-alkylene can be replaced by $C=O$, $(C=O)O$, $(C=O)NR^{50}$, $SO_2-NR^{50}$, $NR^{50}$, $NR^{50}R^{61}$, O or S, wherein $R^{50}$ and $R^{51}$ are independently from each other and at each occurrence $C_{1-10}$-alkyl.

wherein $R^{50}$ and $R^{51}$ are independently from each other and at each occurrence $C_{1-10}$-alkyl.

Also part of the present invention is a process for the preparation of the compounds of formula (1').

The process for the preparation of the compounds of formula

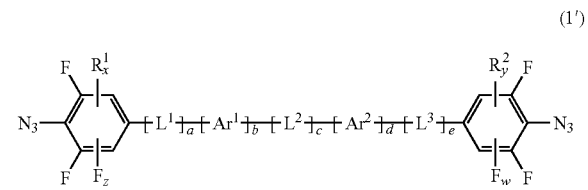

wherein a is 0, 1 or 2, b is 1, 2, 3 or 4, c is 0 or 1, d is 0, 1, 2, 3 or 4, e is 0, 1 or 2, x is 0, 1 or 2, y is 0, 1 or 2, z is 0, 1 or 2, w is 0, 1 or 2, $Ar^1$ and $Ar^2$ are independently from each other and at each occurrence an aromatic or heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$, wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl, wherein $C_{1-20}$-alkyl and $C_{5-8}$-cycloalkyl can be substituted with one or more substituents $R^{aa}$ at each occurrence selected from the group consisting of phenyl, $COOR^{12}$, $CONR^{12}R^{13}$, $COR^{12}$, $SO_3R^{12}$, CN, $NO_2$, halogen, $OR^{12}$, $SR^{12}$, $NR^{11}R^{12}$, $OCOR^{12}$ and $NR^{12}COR^{13}$, wherein $C_{6-14}$-aryl and 5 to 12 membered heteroaryl can be substituted with one or more substituent $R^{ab}$ at each occurrence selected from the group consisting of $C_{1-10}$-alkyl, cyclopentyl, cyclohexyl, $COOR^{12}$, $CONR^{12}R^{13}$, $COR^{12}$, $SO_3R^{12}$, CN, $NO_2$, halogen, $OR^{12}$, $SR^{12}$, $NR^{12}R^{13}$, $OCOR^{12}$ and $NR^{12}COR^{13}$, wherein $R^{12}$ and $R^{13}$ are independently from each other and at each occurrence $C_{1-10}$-alkyl, cyclopentyl, cyclohexyl or phenyl, and wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B, $L^1$ and $L^3$ are independently from each other and at each occurrence

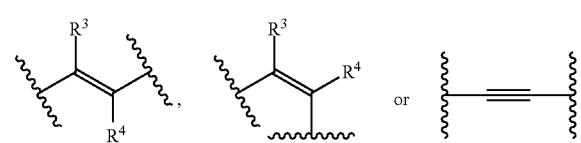

wherein $R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen, wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl,
wherein $C_{1-20}$-alkyl and $C_{5-8}$-cycloalkyl can be substituted with one or more substituents $R^b$ at each occurrence selected from the group consisting of phenyl, $COOR^{22}$, $CONR^{22}R^{23}$, $COR^{22}$, $SO_3R^{22}$, CN, $NO_2$, halogen, $OR^{22}$, $SR^{22}$, $NR^{22}R^{23}$, $OCOR^{22}$ and $NR^{22}COR^{23}$,
wherein $C_{6-14}$-aryl and 5 to 12 membered heteroaryl can be substituted with one or more substituent $R^c$ at each occurrence selected from the group consisting of $C_{1-10}$-alkyl, cyclopentyl, cyclohexyl, $COOR^{22}$, $CONR^{22}R^{23}$, $COR^{22}$, $SO_3R^{22}$, CN, $NO_2$, halogen, $OR^{22}$, $SR^{22}$, $NR^{22}R^{23}$, $OCOR^{22}$ and $NR^{22}COR^{23}$,
wherein $R^{22}$ and $R^{23}$ are independently from each other and at each occurrence $C_{1-10}$-alkyl, cyclopentyl, cyclohexyl or phenyl,
or, if $L^1$ or $L^3$ are

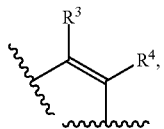

$R^3$ and $R^4$ together with the C-atoms to which they are attached form a 5 to 7-membered non-aromatic ring system A,
$L^2$ is a linking moiety A,
and
$R^1$ and $R^2$ are independently from each other and at each occurrence H, $C_{1-20}$-alkyl, $C_{5-8}$-cycloalkyl, $C_{6-14}$-aryl, 5 to 12 membered heteroaryl, $COOR^{30}$, $CONR^{30}R^{31}$, $COR^{30}$, $SO_3R^{30}$, CN, $NO_2$, halogen, $OR^{30}$, $SR^{30}$, $NR^{30}R^{31}$, $OCOR^{30}$ or $NR^{30}COR^{31}$,
wherein $R^{30}$ and $R^{31}$ are independently from each other and at each occurrence H, $C_{1-20}$-alkyl, $C_{5-8}$-cycloalkyl, $C_{6-14}$-aryl or 5 to 12 membered heteroaryl,
wherein $C_{1-20}$-alkyl and $C_{5-8}$-cycloalkyl can be substituted with one or more substituents $R^d$ at each occurrence selected from the group consisting of phenyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$,
wherein $C_{6-14}$-aryl and 5 to 12 membered heteroaryl can be substituted with one or more substituent $R^e$ at each occurrence selected from the group consisting of $C_{1-10}$-alkyl, cyclopentyl, cyclohexyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$,
wherein $R^{32}$ and $R^{33}$ are independently from each other and at each occurrence $C_{1-10}$-alkyl, cyclopentyl, cyclohexyl or phenyl,
comprises the step of reacting a compound of formula (2)

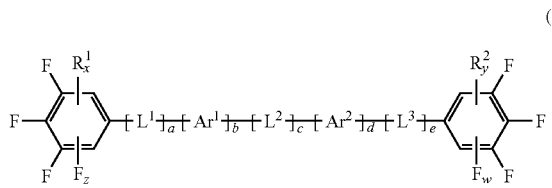

wherein a, b, c, d, e, x, y, z, w, $Ar^1$, $Ar^2$, $L^1$, $L^3$, $L^2$, $R^1$ and $R^2$ are as depicted for the compound of formula (1),
with $M^{m+}(N_3^-)_m$,
wherein m is 1, 2 or 3, and M is a metal,
M can be any metal such as alkaline metal, earth alkaline metal or transition metal. Preferably, the metal is an alkaline metal, more preferably it is sodium.

The reaction is usually performed in a solvent or solvent mixture. Preferably, the reaction is performed in a mixture of water and an organic solvent such as dimethylformamide. The reaction is usually performed at elevated temperatures such as at temperature in the range of 80 to 90° C.

Depending on the type of compound of formula (2), the compound of formula (2) can be prepared by different processes.

Compounds of formula (2), wherein a and e are 1, $L^1$ and $L^3$ are the same and are

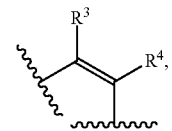

$R^1$ and $R^2$ are the same, x and y are the same, and z and w are the same
can be prepared by reacting a compound of formula (3)

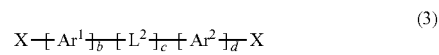

wherein X is halogen, preferably Br, and b, c, d, $Ar^1$, $L^2$, $Ar^2$ are as depicted for the compound of formula (1) with compounds of formula (4A)

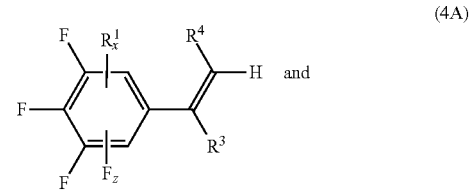

and (4B)

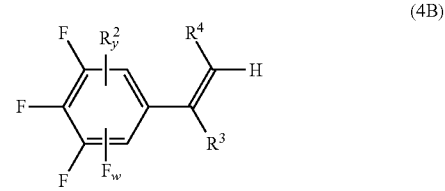

wherein x, y, z, w, $R^1$, $R^2$, $R^3$ and $R^4$ are as depicted for the compound of formula (1), but x and y are the same, z and w are the same and $R^1$ and $R^2$ are the same.

The reaction is usually performed in the presence of a suitable catalyst such as $Pd(OAc)_2$/tri(o-tolyl)phosphine. The reaction is usually performed in a suitable solvent such as dimethylformamide. The reaction is usually performed at elevated temperatures such as at a temperature in the range of 80 to 110° C.

Compounds of formula (2), wherein a and e are 0, $R^1$ and $R^2$ are the same, x and y are the same, and z and w are the same can be prepared by reacting a compound of formula

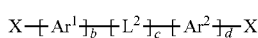 (3)

wherein X is halogen, preferably Br, and b, c, d, Ar¹, L², Ar² are as depicted for the compound of formula (1) with compounds of formula

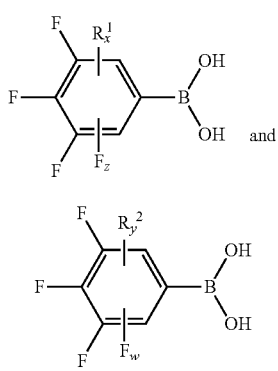

(5A) and (5B)

wherein x, y, z, w, R¹ and R² are as depicted for the compound of formula (1), but x and y are the same, z and w are the same and R¹ and R² are the same.

The reaction is usually performed in the presence of a suitable catalyst such as $Pd(PPh_3)_4$ and $Ag_2O$. The reaction is usually performed in a suitable solvent such as dimethylformamide. The reaction is usually performed at elevated temperatures such as at a temperature in the range of 70 to 110° C.

Compounds of formula (2), wherein a and e are 1, L¹ and L³ are the same and are

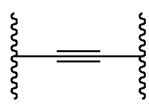 [SMILES: *C#C*]

R¹ and R² are the same, x and y are the same, and z and w are the same can be prepared by reacting a compound of formula

 (6)

wherein b, c, d, Ar¹, L², Ar² are as depicted for the compound of formula (1) with compounds of formula

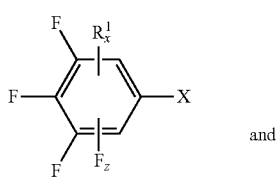

(8A) and (8B)

wherein X is halogen, preferably Br, x, y, z, w, R¹ and R² are as depicted for the compound of formula (1), but x and y are the same, z and w are the same and R¹ and R² are the same.

The reaction is usually performed in the presence of a suitable catalyst such as $Pd(PPh_3)_2Cl_2$ and CuI. The reaction is usually performed in a suitable solvent. The reaction is usually performed at elevated temperatures such as at a temperature in the range of 60 to 100° C.

The compound of formula (6) can be prepared by treating a compound of formula

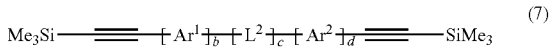 (7)

wherein b, c, d, Ar¹, Ar² and L² are as depicted for the compound of formula (1) with a base.

The base can be potassium hydroxide. The reaction is usually performed in a suitable solvent such as tetrahydrofuran and methanol. The reaction is usually performed at ambient temperatures such as at a temperature in the range of 15 to 30° C.

The compounds of formula (7 can be prepared by reacting a compound of formula

 (3)

wherein b, c, d, Ar¹, Ar² and L² are as depicted for the compound of formula (1)
with ethynyltrimethylsilane.

The reaction is usually performed in the presence of a suitable catalyst such as $Pd(PPh_3)_2Cl_2$ and CuI. The reaction is usually performed in a suitable solvent. The reaction is usually performed at elevated temperatures such as at a temperature in the range of 60 to 100° C.

The compounds of formula (3), wherein Ar¹ and Ar² are the same, b and d are 1, c is 1, X is Br and L² are as depicted for a compound of formula (1) can be prepared by reacting a compound of formula

 (9A)

and

 (9B)

with a compound of formula

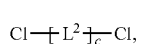 (8)

wherein c is 1 and $L^2$ is as depicted for a compound of formula (1).

Also part of the present invention is a solution comprising one or more compounds of formula (1), one or more polymers and one or more solvents.

A polymer is defined as a compound comprising at least two repeating units. Preferably, the polymer has a molecular weight of from 10'000 Da to 30 million Da. More, preferably, the polymer has a molecular weight of from 20'000 Da to 10 million Da.

The polymer can be any polymer suitable for use in an electronic device such as a dielectric polymer, a semiconductive polymer, or a polymer suitable for forming a passivation, encapsulation or planarization layer.

Preferably, the polymer is a dielectric polymer.

Examples of dielectric polymers are styrene-based polymers, poly($C_{1-6}$-alkyl methacrylates) such as poly(methyl methacrylate) and poly(ter-butyl methacrylate), poly($C_{1-6}$-alkyl acrylates), and polyimides such as the polyimides described in WO 2012/059386 and PCT/IB2013/052426.

Styrene-based polymers are polystyrene or copolymer comprising styrene units. Examples of styrene-based polymers are polystyrene, poly(4-methoxy-styrene) and styrene-butadiene block copolymers. A preferred styrene-based polymer is polystyrene.

Preferably, the one or more polymers are dielectric polymers. More preferably, the one or more polymers are styrene-based polymers. Most preferably, the one or more polymers are polystyrene.

Examples of semiconducting polymers are polythiophenes such as poly 3-hexylthiophene (P3HT), polyfluorenes, polydiacetylene, poly 2,5-thienylene vinylene, poly p-phenylene vinylene (PPV) and polymers comprising repeating units having a diketopyrrolopyrrole group (DPP polymers).

Preferably the semiconducting material is a polymer comprising units having a diketopyrrolopyrrole group (DPP polymer).

Examples of DPP polymers and their synthesis are, for example, described in U.S. Pat. No. 6,451,459 B1, WO 2005/049695, WO 2008/000664, WO 2010/049321, WO 2010/049323, WO 2010/108873, WO 2010/115767, WO 2010/136353 and WO 2010/136352.

Preferably, the DPP polymer comprises, preferably essentially consists, of a unit selected from the group consisting of a polymer unit of formula

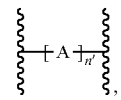

(20)

a copolymer unit of formula

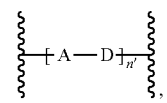

(21)

a copolymer unit of formula

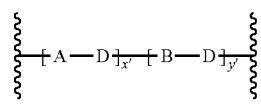

(22)

and a copolymer unit of formula

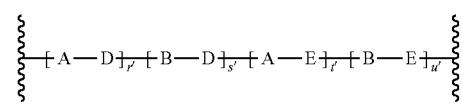

(23)

wherein
n' is 4 to 1000,
x' is 0.995 to 0.005,
y' is 0.005 to 0.995,
x'+y'=1;
r' is 0.985 to 0.005,
s' is 0.005 to 0.985,
t' is 0.005 to 0.985,
u' is 0.005 to 0.985,
r'+s'+t'+u'=1;
A is a group of formula

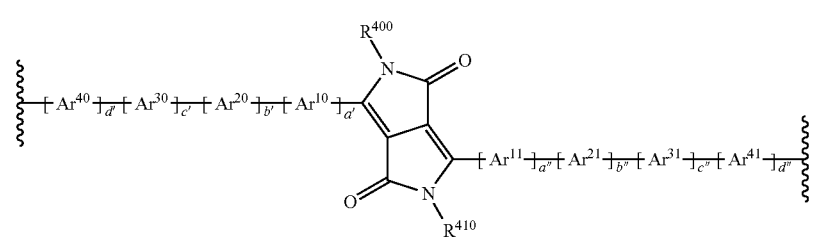

(24)

wherein
a' is 1, 2, or 3,
a" is 0, 1, 2, or 3,
b' is 0, 1, 2, or 3,
b" is 0, 1, 2, or 3,
c' is 0, 1, 2, or 3,
c" is 0, 1, 2, or 3,
d' is 0, 1, 2, or 3,
d" is 0, 1, 2, or 3,
with the proviso that b" is not 0, if a" is 0;
$R^{400}$ and $R^{410}$ are independently from each other selected from the group consisting of H, $C_{1-30}$-alkyl, $C_{5-8}$-cycloalkyl, $C_{6-14}$-aryl, $COOR^{500}$ and $C(O)NH_2$,
   wherein $R^{500}$ is $C_{1-30}$-alkyl,
   wherein $C_{1-30}$-alkyl may be substituted with one or more $R^k$ at each occurrence selected from the group consisting of halogen, OH, $NO_2$, CN, $C_{6-14}$-aryl and $C_{5-8}$-cycloalkyl; and/or interrupted by O, COO, OCO or S,
   wherein $C_{5-8}$-cycloalkyl and $C_{6-14}$-aryl may be substituted with one or more $R^1$ at each occurrence selected from the group consisting of $C_{1-10}$-alkyl, O—$C_{1-10}$-alkyl, S—$C_{1-10}$-alkyl and halogen,
$Ar^{10}$, $Ar^1$, $Ar^{20}$, $Ar^{21}$, $Ar^{30}$, $Ar^{31}$, $Ar^{40}$ and $Ar^{41}$ are independently from each other a heteroaromatic or aromatic ring system,
B, D and E are independently of each other a group of formula

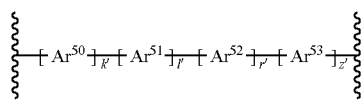

(25)

or a group of formula (24),
with the proviso that in case B, D and E are a group of formula (24), they are different from A, wherein
k' is 1,
l' is 0, or 1,
r' is 0, or 1,
z' is 0, or 1, and
$Ar^{51}$, $Ar^{52}$, $Ar^{53}$ and $Ar^{54}$ are independently from each other a group of formula

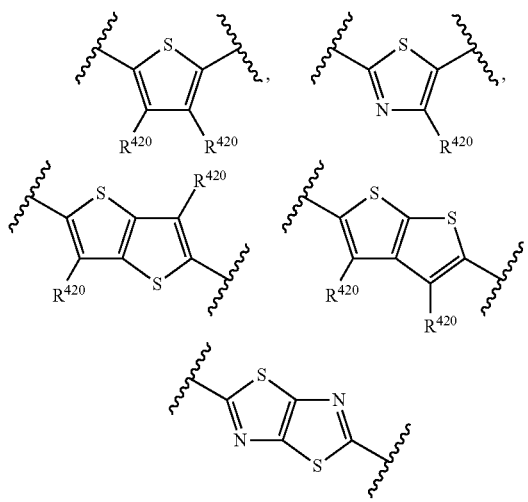

wherein
$R^{420}$ at each occurrence is H or $C_{1-30}$-alkyl, wherein $C_{1-30}$-alkyl may be interrupted by one or more O.
Preferably,
n' is 4 to 200, more preferably 5 to 100,
x' is 0.2 to 0.8,
y' is 0.8 to 0.2, and
x'+y'=1.
Preferably, $Ar^{10}$, $Ar^{20}$, $Ar^{30}$, $Ar^{40}$, $Ar^{11}$, $Ar^{21}$, $Ar^{31}$ and $Ar^{41}$ are independently from each other heteroaromatic or aromatic ring systems selected from the group consisting of

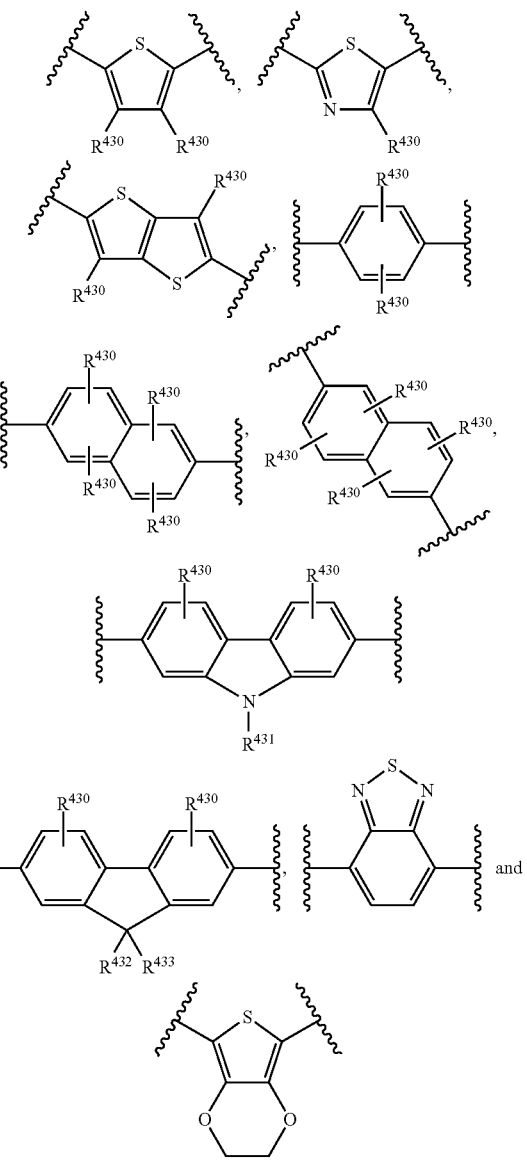

wherein
$R^{430}$ is at each occurrence H, $C_{1-30}$-alkyl, halogen or O—$C_{1-30}$-alkyl,
   wherein $C_{1-30}$-alkyl may be substituted with one or more $C_{6-14}$-aryl or $C_{5-8}$-cycloalkyl, and/or interrupted by one or more O or S,
$R^{431}$ is $C_{1-30}$-alkyl, $C_{1-14}$-aryl, O—$C_{1-30}$-alkyl or $COOR^{440}$, wherein $R^{440}$ is $C_{1-30}$-alkyl,
wherein $C_{1-30}$-alkyl may be substituted with phenyl, halogen or $COOR^{441}$, and/or interrupted by one or more O or S,
wherein $C_{6-14}$-aryl may be substituted with $C_{1-10}$-alkyl, $C_{1-10}$-perhalogenoalkyl or $OC_{1-10}$-alkyl, and
$R^{432}$ and $R^{433}$ are independently from each other H, $C_{1-30}$-alkyl, $C_{6-14}$-aryl, 5 to 12 membered heteroaryl, $C_{2-10}$-alkenyl, $C_{2-10}$-alkynyl or $O-C_{1-30}$-alkyl,
wherein $C_{1-30}$-alkyl and $O-C_{1-30}$-alkyl may be substituted with one or more substituents $R^m$ at each occurrence selected from the group consisting of phenyl, $S-C_{1-10}$-alkyl, $O-C_{1-10}$-alkyl, CN, $NR^{441}R^{442}$, $CONR^{441}R^{442}$ and halogen; and/or interrupted by one or more CO, COO, S, O or $NR^{443}$,
wherein $C_{6-14}$-aryl and 5 to 12 membered heteroaryl may be substituted with one or more substituents $R^n$ at each occurrence selected from the group consisting of $C_{1-10}$-alkyl, $S-C_{1-10}$-alkyl, $O-C_{1-14}$-alkyl, CN, $NR^{441}R^{442}$, $CONR^{441}R^{442}$ and halogen;
wherein $R^{441}$, $R^{442}$ and $R^{443}$ are independently from each other H, $C_{1-10}$-alkyl or phenyl,
or
$R^{432}$ and $R^{433}$ together form a group of formula $CR^{450}R^{451}$, wherein $R^{450}$ and $R^{451}$ are independently from each other H, $C_{1-30}$-alkyl, $C_{6-14}$-aryl or 5 to 12 membered heteroaryl,
wherein $C_{1-30}$-alkyl may be substituted with one or more substituents RP at each occurrence selected from the group consisting of phenyl, $S-C_{1-10}$-alkyl, $O-C_{1-10}$-alkyl, CN, $NR^{452}R^{453}$, $CONR^{452}R^{453}$ and halogen; and/or interrupted by one or more CO, COO, S, O or $NR^{454}$,
wherein $C_{6-14}$-aryl and 5 to 12 membered heteroaryl may be substituted with one or more substituents $R^q$ at each occurrence selected from the group consisting of $C_{1-10}$-alkyl, $S-C_{1-10}$-alkyl, $O-C_{1-10}$-alkyl, CN, $NR^{452}R^{453}$, $CONR^{452}R^{453}$ and halogen;
wherein $R^{452}$, $R^{453}$ and $R^{44}$ are independently from each other H, $C_{1-10}$-alkyl or phenyl,
or
$R^{432}$ and $R^{433}$ together with the C-atom, to which they are attached, form a five or six-membered ring, wherein the five to six-membered ring may be substituted with one or more substituents $R^r$ selected from the group consisting of $C_{1-30}$-alkyl, $C_{6-14}$-aryl, 5 to 12 membered heteroaryl, $C_{2-10}$alkenyl, $C_{2-10}$-alkynyl and $O-C_{1-30}$-alkyl,
wherein $C_{1-30}$-alkyl and $O-C_{1-30}$-alkyl may be substituted with one or more substituents $R^s$ at each occurrence selected from the group consisting of phenyl, $S-C_{1-10}$-alkyl, $O-C_{1-10}$-alkyl, CN, $NR^{460}R^{461}$, $CONR^{460}R^{461}$ and halogen; and/or interrupted by one or more CO, COO, S, O or $NR^{462}$, wherein $C_{6-14}$-aryl and 5 to 12 membered heteroaryl may be substituted with one or more substituents $R^t$ at each occurrence selected from the group consisting of $C_{1-10}$-alkyl, $S-C_{1-10}$-alkyl, $O-C_{1-10}$-alkyl, CN, $NR^{460}R^{461}$, $CONR^{460}R^{461}$ and halogen;
wherein $R^{460}$, $R^{461}$ and $R^{462}$ are independently from each other H, $C_{1-10}$-alkyl or phenyl.
More preferably, the DPP polymer comprises, preferably essentially consists, of a unit selected from the group consisting of a polymer unit of formula

(20)

wherein
n' is 4 to 100, and
A is a group of formula

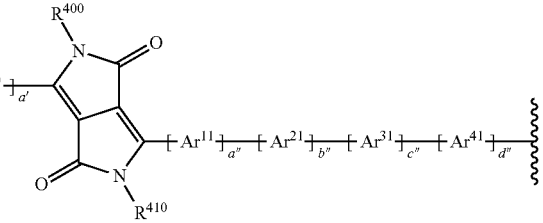
(24)

wherein
a' is 1,
a" is 2
b', b", c', c", d' and d" are 0,
$R^{400}$ and $R^{410}$ are independently from each other $C_{1-30}$-alkyl, and
$Ar^{10}$ and $Ar^{11}$ are heteroaromatic or aromatic ring systems, which are

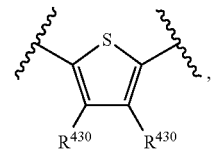

wherein
$R^{430}$ is at each occurrence H.
Preferably, the solution comprises one or more compounds of formula (1), one or more polymers and one or more solvents, wherein the solution comprises
i) 0.1 to 500 mg of the one or more polymers in 1 ml of the composition, and
ii) 0.1 to 20% by weight of the one or more compounds of formula (1) based on the weight of the one or more polymers.
More preferably, the solution comprises one or more compounds of formula (1), one or more polymers and one or more solvents, wherein the solution comprises i) 1.0 to 250 mg of the one or more polymers in 1 ml of the composition, and
ii) 0.5 to 15% by weight of the one or more compounds of formula (1) based on the weight of the one or more polymers.

Most preferably, the solution comprises one or more compounds of formula (1), one or more polymers and one or more solvents, wherein the solution comprises
i) 5 to 100 mg of the one or more polymers in 1 ml of the composition, and
ii) 1 to 10% by weight of the one or more compounds of formula (1) based on the weight of the one or more polymers.

In particular, the solution comprises one or more compounds of formula (1), one or more polymers and one or more solvents, wherein the solution comprises
i) 5 to 60 mg of the one or more polymers in 1 ml of the composition, and
ii) 2 to 8% by weight of the one or more compounds of formula (1) based on the weight of the one or more polymers.

If the polymer is polystyrene, the solvent is preferably a $C_{1-10}$-alkyl $C_{1-10}$-alkanoat such as butyl acetate.

If the polymer is a DPP polymer, the solvent is preferably an aromatic solvent such as toluene.

Also part of the present invention is a process for the preparation of a device which process comprises the steps of (i) depositing the solution of the present invention on a support in order to form a layer, and (ii) exposing the layer of step (i) to radiation in order to form a polymer layer.

Preferably, the device is an electronic device. Examples of electronic devices are light emitting diode (LED) devices, field effect transistor (FET) devices, photovoltaic (PV) devices, photodetector devices, sensing devices and radio-frequency identification (RFID) tags.

More preferably, the device is a light emitting diode (LED) device, a field effect transistor (FET) device or a photovoltaic (PV) device.

Most preferably, the device is a field effect transistor (FET) device.

A field effect transistor (FET) device comprises a dielectric layer, a semiconducting layer, a substrate, gate electrodes and source/drain electrodes.

If the device of the present invention is a field effect transistor (FET) device, the polymer layer may be the semiconducting layer or the dielectric layer. Preferably, it is the dielectric layer.

If the polymer layer is the dielectric layer, the semiconducting layer of the polymer field effect transistor (FET) device can be formed from one or more semiconducting polymers mentioned above or alternatively from small molecules. Preferably, it is formed from one or more DPP polymers.

If the polymer layer is the semiconducting layer, the dielectric layer of the field effect transistor (FET) device can be formed from one or more dielectric polymers mentioned above or alternatively from small molecules. Preferably, it is formed from one or more styrene-based polymers.

The dielectric layer can have a thickness of 5 to 2000 nm, preferably of 10 to 1000 nm. The semiconducting layer can have a thickness of 5 to 2000 nm, preferably of 10 to 1000 nm.

The substrate can be any suitable substrate such as glass, or a plastic substrate such as polyethersulfone, polycarbonate, polysulfone, polyethylene terephthalate and polyethylene naphthalate.

The gate electrodes as well as the source/drain electrodes can be formed from any suitable metal such as gold, silver, tantalum, aluminium, tungsten or indium tin oxide. The gate electrodes as well as the source/drain electrodes can have a thickness of 1 to 200 nm, preferably from 5 to 100 nm.

A field effect transistor (FET) device can have various designs.

One possible design of a field effect transistor (FET) device is the bottom-gate, bottom-contact design. This design is depicted in FIG. 9.

Another possible design of a field effect transistor (FET) device is the top-gate, bottom-contact design. This design is depicted in FIG. 10.

The support depends on the and on the one or more polymers of the solution of the present invention.

If the device is a top gate, bottom contact polymer field effect transistor (FET) device and the one or more polymers are dielectric polymers, the support is the semiconducting layer of the FET.

If the device is a top gate, bottom contact polymer field effect transistor (FET) device and the one or more polymers are semiconducting polymers, the support is the substrate of the FET.

The solution of the present invention can be deposited on the support in various ways. Preferably, the solution is deposited by way of liquid processing techniques such as spin coating, solution casting, ink-jet, flexo-printing, gravure printing or slot die coating.

Preferably, the layer of step (i) is heated to a temperature in the range of 50 to 150° C. before step (ii). More preferably, the layer of step (i) is heated to a temperature in the range of 80 to 130° C. before step (ii).

Preferably, the radiation of step (ii) has a wavelength in the range of 300 to 450 nm. For example, the radiation can have a wavelength of 365 nm, 405 nm or 436 nm.

The radiation dosage of the radiation used in step (ii) can be in the range of 1 to 1000 $mJ/cm^2$, Preferably it is in the range of 5 to 300 $mJ/cm^2$, most preferably in the range of 10 to 100 $mJ/cm^2$.

Step (ii) can be performed under inert gas atmosphere such as nitrogen or argon atmosphere.

A temperature in the range of 50 to 150°, in particular in the range of 80 to 130° C., can be applied during step (ii).

For example, if the polymer layer is the dielectric layer and the device is a top-gate, bottom contact field effect transistor (FET) device, the device can be prepared as follows: The source and drain electrodes can be formed by lithographically patterning a suitable source/drain material, for example gold, on a suitable substrate, for example glass. The source/drain electrodes can then be covered with a semiconducting layer by spin-coating a solution of a semiconducting polymer, for example a DPP polymer, in a suitable solvent, for example toluene, on the substrate. The wet semiconducting layer can be heated. The semiconducting layer can then be covered with a dielectric layer by spin-coating a solution comprising one or more compounds of formula (1) of the present invention, one or more dielectric polymers, for example polystyrene, in a suitable solvent, for example butyl acetate, on the semiconducting layer. The wet dielectric layer can be heated to 80 to 100° C., and then cured by radiation. The gate electrode can then be deposited on the dielectric layer for example by vapour deposition of a suitable source/drain material, for example gold.

Also part of the present invention is a device obtainable by the process of the present invention.

Also part of the invention is the use of the compounds of formula (1) as cross-linkers for cross-linking one or more polymers.

The compounds of formula (1) of the present invention are advantageous in that the compounds of formula (1) absorb at a wavelength in the range of 300 to 450 nm. In particular, the compounds can be activated at a wavelength of 365 nm, 405 nm or 436 nm, which are the wavelengths currently used in industrial photolithography processes used in the preparation of devices such as control field effect transistors (FET) for displays. The compounds of formula (1) allow the preparation of devices using the same wavelength for the photolithography as well as for the crosslinking of the polymer layer. Thus, there is no need to adjust the wavelength of the photo-device or even to replace the photo-device by a radiation device suitable for cross-linking the polymer during the preparation process of the device.

The compounds of formula (1) are advantageous in that they are efficient cross-linkers at wavelengths in the range of 300 to 450 nm, even when using a low radiation dosage, for example a radiation dosage in the range of 5 to 300 mJ/cm$^2$ or in the range of 10 to 100 mJ/cm$^2$. The compounds of formula (1) are in particular efficient cross-linkers for dielectric layers such as polystyrene-based polymer layers. After cross-linking the polymer layer is almost not soluble in the solvent anymore used for applying the layer. Thus, the next layer, for example an electrode material layer or barrier layer, can be applied without dissolving the polymer layer. The efficient cross-linking of the compounds of formula (1) also allows the structuring (patterning) of the polymer layer using a photo-mask.

In addition, the compounds of formula (1) are soluble in organic solvents and organic solvents are usually used in the preparation of devices. Depending on the polymer layer to be applied, the compounds of formula (1) can be selected in order to be soluble in the solvent used for the polymer layer to be applied. For example, if the solvent is a more polar organic solvent such as butyl acetate, a compound of formula (1) is ideally selected, wherein $Ar^1$ and $Ar^2$ are substituted with one or more substituent $C_{1-20}$-alkyl in order to increase the solubility in the more polar organic solvent.

EXAMPLE 1

Preparation of Compound 1a

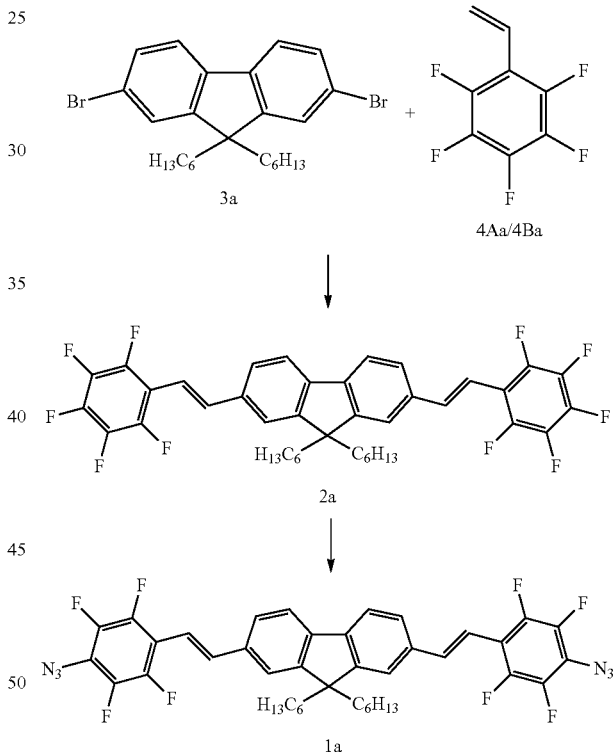

Preparation of Compound 2a

Figure 1:
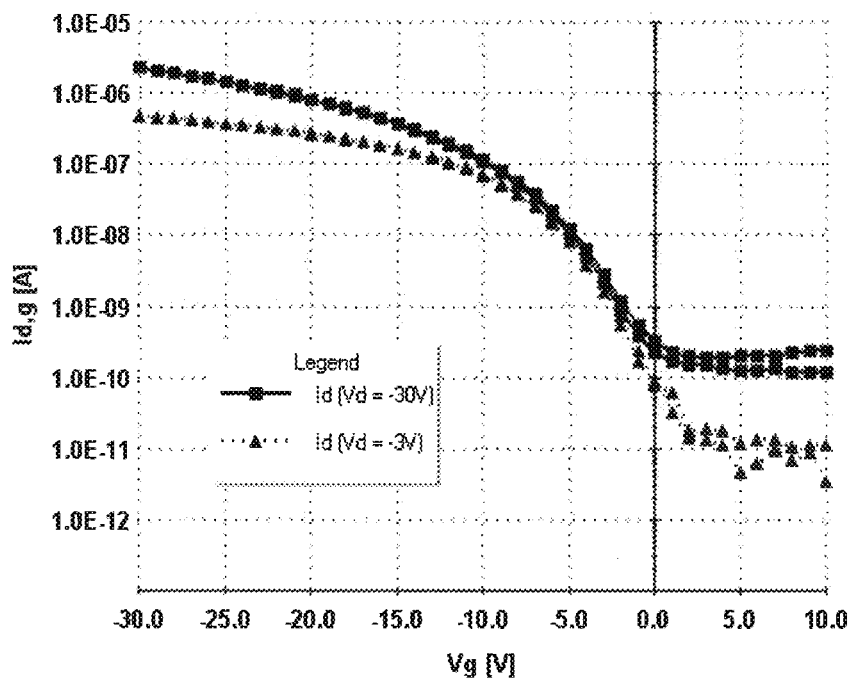
FIG. 1 shows the drain current $I_{ds}$ in relation to the gate voltage $V_{gs}$ (transfer curve) for the top-gate, bottom-contact (TGBC) field effect transistor of example 6 comprising a dielectric layer formed from Formulation B at a source voltage $V_{ds}$ of −3V (triangle), respectively, −30V (square).

A mixture of 2,7-dibromo-9,9-dihexyl-9H-fluorene (3a) (492 mg, 1.00 mmol), 2,3,4,5,6,-pentafluorostyrene (4Aa/4Ba) (524 mg, 2.7 mmol), P(o-tolyl)$_3$ (12 mg, 0.04 mmol) and Pd(OAc)$_2$ (4.5 mg, 0.02 mmol) in triethylamine (0.87 mL) was heated at 90° C. for 1 day under N$_2$. The reaction mixture was cooled to room temperature and extracted with dichloromethane (3×15 mL), The organic layer was finally washed with water (3×30 mL). The organic phase was then dried over MgSO$_4$ and evaporated under reduced pressure. The crude product was purified by column chromatography using hexane as the eluent to yield compound 2a as pale yellow solid (370 mg, 64%).

Preparation of Compound 1a

A mixture of NaN$_3$ (73 mg, 1.1 mmol) and compound 2a (367 mg, 0.5 mmol) in DMF (9.0 mL) and water (1.4 mL) was heated at 90° C. until no more starting material was monitored by TLC.

The reaction mixture was cooled to room temperature, diluted with water, extracted with ethyl acetate and washed with water (3×30 mL). The organic layer was dried over MgSO$_4$ and the solvent removed under reduced pressure. The solid was purified by column chromatography (dichloromethane:hexane 5:95) to yield compound 1a as orange solid (115 mg, 35%). $\lambda_{max}$=386 and 408 nm.

EXAMPLE 2

Preparation of Compound 1b

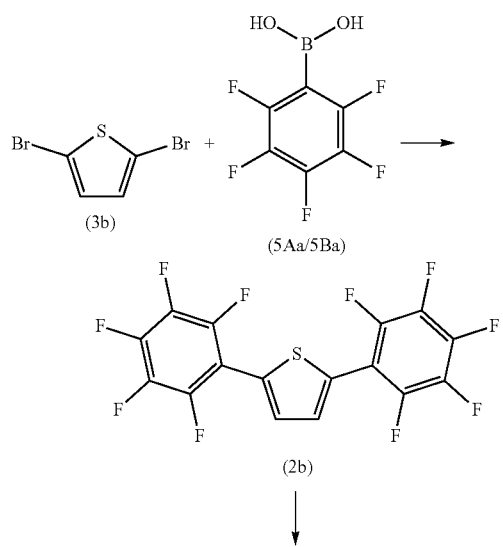

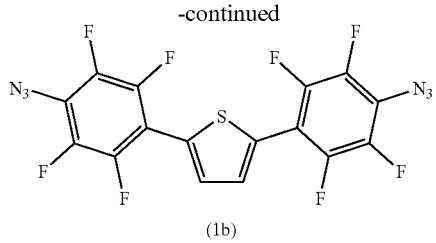

(1b)

Preparation of Compound 2b

A mixture of 2,5-dibromothiophene (3b) (1.0 g, 4.1 mmol), 2,3,4,5,6-pentafluorophenylboronic acid (5Aa/5Ba) (2.1 g, 10.3 mmol), Pd(PPh$_3$)$_4$ (763 mg, 0.7 mmol), Ag$_2$O (1.9 g, 8.2 mmol) and K$_3$PO$_4$ trihydrate (7.025 g) in DMF (30 mL) was stirred at 85° C., overnight. The mixture was then filtered through Celite, poured into water and extracted with dichloromethane (3×25 mL). The combined organic layers were washed with water (3 times), dried over MgSO$_4$ and the solvent was removed under reduced pressure. The crude product was purified by column chromatography using hexane as eluent to yield compound 2b as white powder (767 mg, 45%).

Preparation of Compound 1b

A mixture of NaN$_3$ (171 mg, 2.6 mmol) and compound 2b (500 mg, 1.2 mmol) in DMF (20 mL) and water (3 mL) was heated at 90° C. The reaction was monitored by TLC. The mixture was cooled to room temperature, diluted with water, extracted with ethyl acetate and washed with water (3×25 mL). The extract was dried over MgSO$_4$ and the solvent removed under reduced pressure. The crude product was purified by column chromatography with gradient elution (hexane to hexane/dichloromethane 75:25) to yield compound 1b as a brownish-orange solid (382 mg, 69%). $\lambda_{max}$=386 nm.

EXAMPLE 3

Preparation of Compound 1c

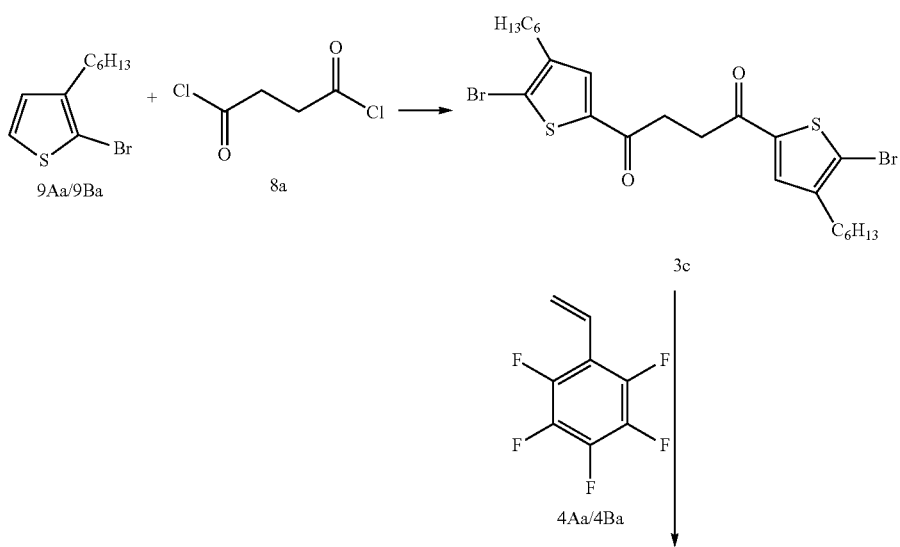

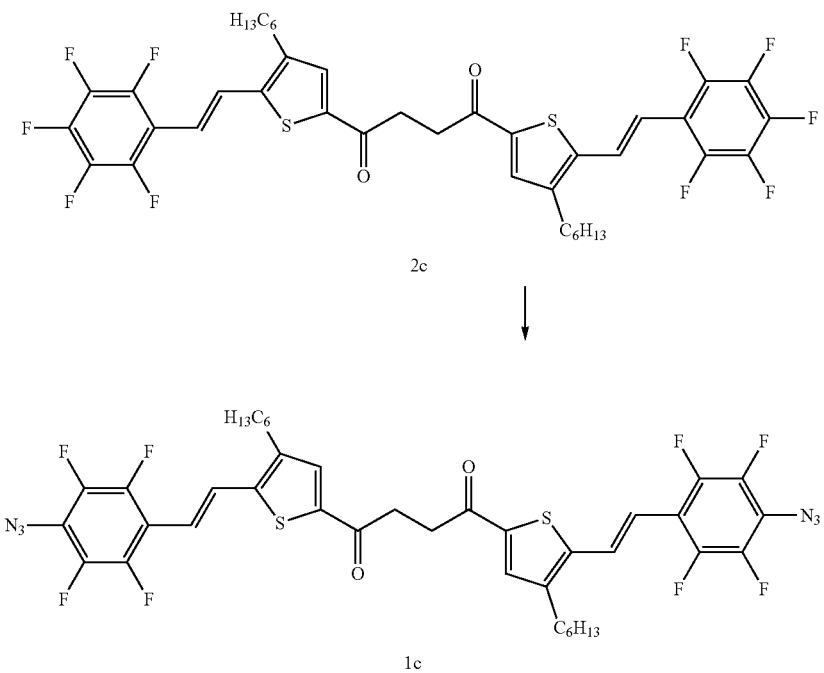

2c

↓

1c

Preparation of Compound 3c

A mixture of 2-bromo-3-hexylthiophene (9Aa/9Ba) (3.0 mL, 14.8 mmol) and succinyl chloride (8a) (0.73 mL, 6.4 mmol) in anhydrous DCM (5 mL) was added dropwise to a cooled (0° C.) suspension of AlCl$_3$ (2.1 g, 15.5 mmol) in anhydrous DCM (5 mL). The reaction mixture was then stirred at room temperature for 2.5 h and finally refluxed for 30 mins. The reaction mixture was poured into ice followed by addition of concentrated HCl and stirred for 1 h. The aqueous layer was extracted with DCM (3×30 mL), washed with HCl solution (10%), water, and saturated NaHCO$_3$ solution. Finally, the organic layer was dried over Na$_2$SO$_4$ and the solvent removed under reduced pressure. The crude solid was purifies by washing with hot ethanol giving compound 3c as orange solid (0.87 g, yield: 30%).

Preparation of Compound 2c

A mixture of compound 3c (0.6 g, 1.0 mmol), 2,3,4,5,6-pentafluorostyrene (4Aa/4Ba) (0.4 mL, 2.7 mmol, Pd(OAc)$_2$ (6 mg, 0.02 mmol) and tri(o-tolyl)phosphine (0.015 g, 0.05 mmol) in triethylamine (1.18 mL, 8.50 mmol) and DMF (3 mL) was heated at 90° C. overnight. The reaction was monitored by TLC and LC/MS and heated until no more starting material was observed. Triethylamine was removed under reduced pressure and the reaction mixture was extracted with DCM (3×30 mL). The organic layer was washed with water (100 mL) and brine (100 mL), dried over MgSO$_4$ and the solvent removed under reduced pressure. The crude was purified by column chromatography using hexane/DCM (1:1) as eluent giving compound 2c as orange solid (0.17 g, yield 26%).

Preparation of Compound 1c

Compound 2c (150 mg, 0.2 mmol) was dissolved in DMF (3.50 mL) and sodium azide (90 mg, 1.5 mmol) in water (0.50 mL) was subsequently added. The reaction mixture was heated at 90° C. for 3 h and monitored by TLC. Water was added to the reaction mixture which was extracted with ethyl acetate (3×25 mL) and dried over MgSO$_4$. After removing the solvent under reduced pressure, the crude product was purified by column chromatography DCM/methanol (10:1) as eluent. Finally, compound 1c was precipitated in hexane obtaining a red precipitate. The solid was filtered on a Buchner filter in to yield compound 1c in 20% yield. $\lambda_{max}$=405 nm

EXAMPLE 4

Preparation of Compound 1d

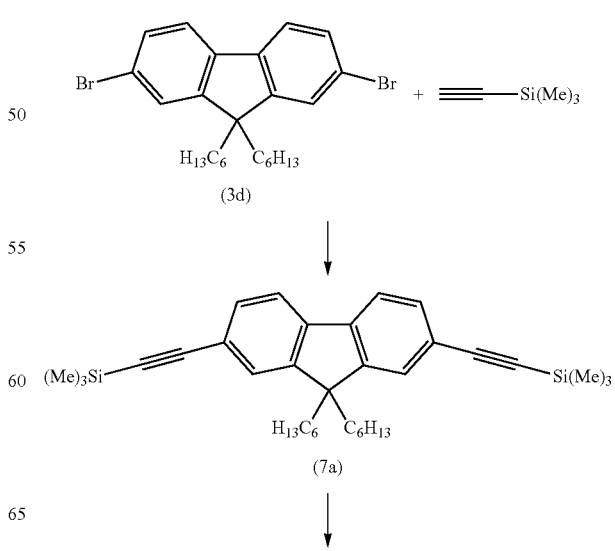

(3d)

↓

(7a)

↓

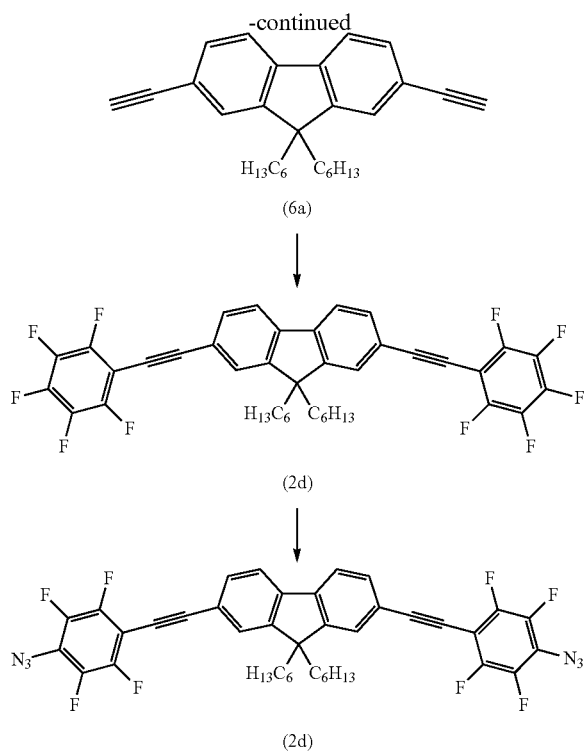

Preparation of Compound 7a

A solution of ethynyltrimethylsilane (0.60 mL, 4.25 mmol) in triethylamine (8 mL) was slowly added to a solution of compound 3d (1.0 g, 1.93 mmol), (PPh$_3$)$_2$PdCl$_2$ (0.068 g, 0.10 mmol), and copper iodide (0.02 g, 0.10 mmol) in triethylamine (20 mL). The resulting mixture was heated at 70° C., overnight. The reaction was monitored by TLC using hexanes as the eluent. Work up: triethylamine was evaporated under reduced pressure and the residue was purified by column chromatography over silica gel, giving compound 7a as yellow solid in 95% yield (0.97 g, 1.8 mmol).

Preparation of Compound 6a

A 20% KOH aqueous solution (2.50 mL) was diluted with methanol (10 mL) and added to a solution of compound 7a (0.97 g, 1.75 mmol) in THF (18 mL). The reaction mixture was then stirred at room temperature until no more starting material was observed by TLC (eluent hexanes). The crude reaction mixture was extracted with hexane (3×15 mL) and the organic phase was washed with water (1×25 mL), and dried over Na$_2$SO$_4$. After removing the solvent under reduced pressure, the residue was then purified by column chromatography using hexanes as the eluent, giving compound 6a as yellow oil in quantitative yield (0.7 g, 1.8 mmol) that was directly used in the following step without any further purification.

Preparation of Compound 2d

A solution of compound 6a (0.20 g, 0.50 mmol) in triethylamine (1 mL) was slowly added to a solution of bromo-pentafluorobenzene (4Aa/4Ba) (0.14 mL, 1.09 mmol), (PPh$_3$)$_2$PdCl$_2$ (0.017 g, 0.02 mmol), and copper iodide (0.005 g, 0.02 mmol) in triethylamine (11 mL). The reaction mixture was then heated at 70° C. overnight and monitored by TLC. Work up: triethylamine was removed under reduced pressure and the residue was purified by column chromatography over silica gel (eluent hexanes), giving compound 2d as white solid in 59% yield (0.21 g, 0.29 mmol).

Preparation of Compound 1d

Sodium azide (0.15 g, 2.30 mmol) in water (1 mL) was added to a DMF solution (5 mL) of compound 2d (0.21 g, 0.29 mmol) and the mixture heated at 90° C. for 3 hrs. Workup: water was added to the reaction mixture which was subsequently extracted with ethyl acetate (3×10 mL). The organic phase were gathered and dried over MgSO$_4$. After removing the solvent under reduced pressure the residue was purified by column chromatography over silica gel (eluent hexanes), giving compound 1d as yellow solid in 50% yield (0.11 g, 0.15 mmol). $\lambda_{max}$=365 nm.

EXAMPLE 5

Preparation of Formulations A, B, C, D and E

Formulation A is a solution of 40 mg/ml polystyrene (Mw~2,000,000, supplied by Pressure Chemicals) in butyl acetate/toluene (23/2 by volume) containing in addition 2% by weight of compound 1b based on the weight of polystyrene. Compound 1b is prepared as described in example 2.

Formulation B is a solution of 40 mg/ml polystyrene (Mw~2,000,000, supplied by Pressure Chemicals) in butyl acetate containing in addition 4% by weight of compound 1a based on the weight of polystyrene. Compound 1a is prepared as described in example 1.

Formulation C is a solution of 40 mg/ml polystyrene (Mw~2,000,000, supplied by Pressure Chemicals) in butyl acetate containing in addition 4% by weight of compound 1d based on the weight of polystyrene. Compound 1d is prepared as described in example 4.

Formulation D is a solution of 20 mg/ml of the diketopyrrolopyrrole (DPP)-thiophene-polymer of example 1 of WO 2010/049321 in toluene containing in addition 4% by weight of compound 1b based on the weight of the diketopyrrolopyrrole (DPP)-thiophene-polymer. Compound 1b is prepared as described in example 2.

Formulation E is a solution of 0.75% by weight of the diketopyrrolopyrrole (DPP)-thiophene-polymer of example 1 of WO 2010/049321 in toluene containing in addition 4% by weight of compound 1b based on the weight of diketopyrrolopyrrole (DPP)-thiophene-polymer. Compound 1b is prepared as described in example 2.

Formulations A to E were prepared by mixing polystyrene and the diketrroloolopyrrole (DPP)-thiophene-polymer, respectively, and the crosslinker in the solvent at room temperature.

EXAMPLE 6

Preparation of a Top-Gate, Bottom Contact Field Effect Transistor (FET) Device Comprising a Dielectric Layer Formed from Formulation B Gold was deposited by thermal evaporation through a shadow mask onto a glass substrate to form an approximately 60 nm thick film of source/drain electrodes (channel length: 50 μm, channel width: 500 μm). A 0.75% by weight solution of the diketopyrrolopyrrole (DPP)-thiophene-polymer of example 1 of WO 2010/049321 in toluene was filtered through a 0.45 micrometer polytetrafluoroethylene (PTFE) filter and then applied by spin coating (1000 rpm, 30 seconds). The wet semiconducting layer was dried at 90° C. on a hot plate for 30 seconds. Formulation B described in example 5 was filtered through a 0.45 micrometer filter and then applied by spin coating (3000 rpm, 30 seconds). The wet dielectric layer was pre-baked at 90° C. for 2 minutes on a hot plate to obtain a 520 nm thick layer. The polymer dielectric layer was UV-cured using 365 nm (radiation dosage 960 mJ/cm$^2$) at 90° C. Gate electrodes of gold (thickness approximately 80 nm) were evaporated through a shadow mask on the dielectric layer.

Figure 2:
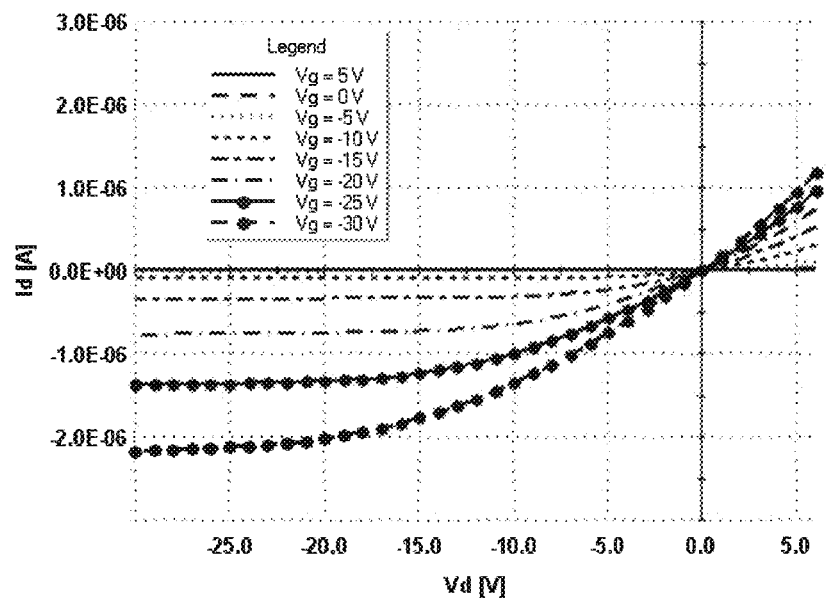
FIG. 2 shows the drain current $I_{ds}$ in relation to the drain voltage $V_{ds}$ (output curve) for the top-gate, bottom-contact (TGBC) field effect transistor of example 6 comprising a dielectric layer formed from Formulation B at a gate voltage $V_{gs}$ of 5V, 0 V, −5 V, −10 V, −15 V, −20V, −25V and −30 V.

The characteristics of the top gate, bottom contact field effect transistor (FET) device were measured with a Keithley 4200-SCS semiconductor characterization system. The drain current $I_{ds}$ in relation to the gate voltage $V_{gs}$ (transfer curve) for the device comprising a dielectric layer formed from Formulation B at a source voltage $V_{ds}$ of −3V (triangle), respectively, −30V (square) is shown in FIG. 1. The drain current $I_{ds}$ in relation to the drain voltage $V_{ds}$ (output curve) for the device comprising a dielectric layer formed from Formulation B at a gate voltage $V_{gs}$ of 5V, 0 V, −5 V, −10 V, −15 V, −20V, −25V and −30 V is shown in FIG. 2.

The results are depicted in table 1.

TABLE 1

| dielectric layer formed from | Mean mobility [cm²/Vs] | Mean $I_{on}/I_{off}$ | Mean $V_{on}$ [V] | Ig [@ 30 V] |
|---|---|---|---|---|
| Formulation B | 0.135 | 1.13E+04 | 2 | 3.31E−08 |

EXAMPLE 7

Preparation of a Top-Gate, Bottom Contact Field Effect Transistor (FET) Device Comprising a Dielectric Layer Formed from Formulation C Gold was deposited by thermal evaporation through shadow mask onto glass substrate to form an approximately 60 nm thick film of source/drain electrodes (channel length: 50 μm, channel width: 500 μm). A 0.75% by weight solution of the diketopyrrolopyrrole (DPP)-thiophene-polymer of example 1 of WO 2010/049321 in toluene was filtered through a 0.45 micrometer polytetrafluoroethylene (PTFE) filter and then applied by spin coating (1000 rpm, 30 seconds). The wet semiconducting layer was dried at 90° C. on a hot plate for 30 seconds. Formulation C described in example 5 was filtered through a 0.45 micrometer filter and then applied by spin coating (3500 rpm, 30 seconds). The wet dielectric layer was pre-baked at 90° C. for 2 minutes on a hot plate to obtain a 520 nm thick layer. The dielectric layer was UV-cured using 365 nm (radiation dosage 1120 mJ/cm²) at 100° C. with nitrogen flow. Gate electrodes of gold (thickness approximately 80 nm) were evaporated through a shadow mask on the dielectric layer.

Figure 3:
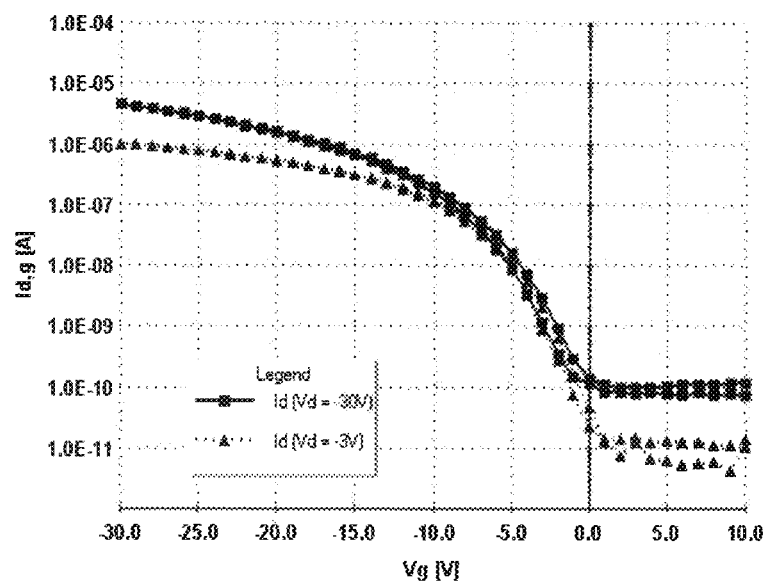
FIG. 3 shows the drain current $I_{ds}$ in relation to the gate voltage $V_{gs}$ (transfer curve) for the top-gate, bottom-contact (TGBC) field effect transistor of example 7 comprising a dielectric layer formed from Formulation C at a source voltage $V_{ds}$ of −3V (triangle), respectively, −30V (square).
Figure 4:
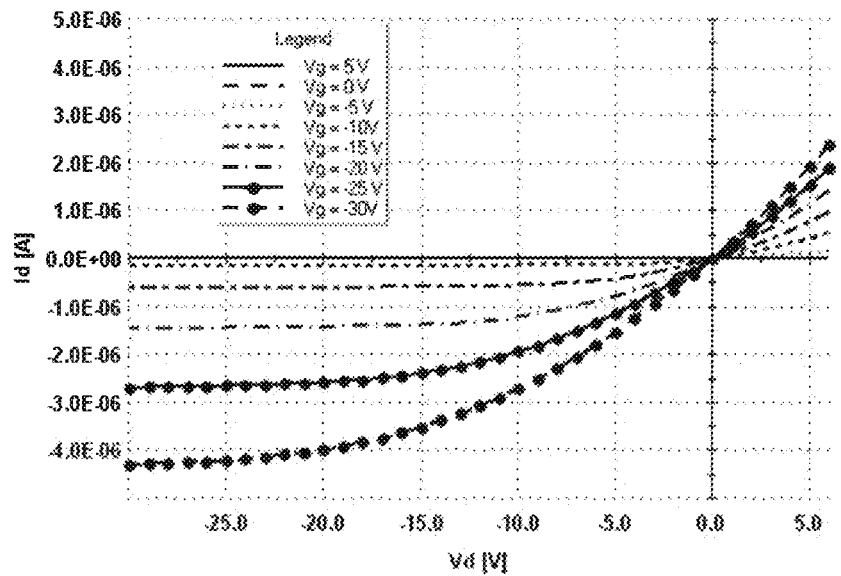
FIG. 4 shows the drain current $I_{ds}$ in relation to the drain voltage $V_{ds}$ (output curve) for the top-gate, bottom-contact (TGBC) field effect transistor of example 7 comprising a dielectric layer formed from Formulation C at a gate voltage $V_{gs}$ of 5V, 0 V, −5 V, −10 V, −15 V, −20V, −25V and −30 V.

The characteristics of the top gate, bottom contact field effect transistor (FET) device were measured with a Keithley 4200-SCS semiconductor characterization system. The drain current $I_{ds}$ in relation to the gate voltage $V_{gs}$ (transfer curve) for the device comprising a dielectric layer formed from Formulation C at a source voltage $V_{ds}$ of −3V (triangle), respectively, −30V (square) is shown in FIG. 3. The drain current $I_{ds}$ in relation to the drain voltage $V_{ds}$ (output curve) for the device comprising a dielectric layer formed from Formulation C at a gate voltage $V_{gs}$ of 5V, 0 V, −5 V, −10 V, −15 V, −20V, −25V and −30 V is shown in FIG. 4.

The results are depicted in table 2.

TABLE 2

| dielectric layer formed from | Mean mobility [cm²/Vs] | Mean $I_{on}/I_{off}$ | Mean $V_{on}$ [V] | Ig [@ 30 V] |
|---|---|---|---|---|
| Formulation C | 0.20 | 3.16E+04 | 1 | 8.67E−09 |

EXAMPLE 8

Preparation of a Top-Gate, Bottom Contact Polymer Field Effect Transistor (FET) Device Comprising a Polymer Semiconducting Layer Formed from Formulation E Gold was deposited by thermal evaporation through shadow mask onto glass substrate to form an approximately 60 nm thick film of source/drain electrodes (channel length: 50 μm, channel width: 500 μm). Formulation E was applied by spin coating (1000 rpm, 30 seconds). The wet polymer semiconducting layer was dried at 90° C. on a hot plate for 30 seconds, and then UV-cured using 365 nm (radiation dosage 2400 mJ/cm²) at 90° C. A 4.0% by weight solution of polystyrene supplied by Pressure Chemicals in butyl acetate was applied by spin coating (3000 rpm, 30 seconds), and dried at 90° C. for 30 seconds. Gate electrodes of gold (thickness approximately 80 nm) were evaporated through a shadow mask on the dielectric layer.

Figure 5:
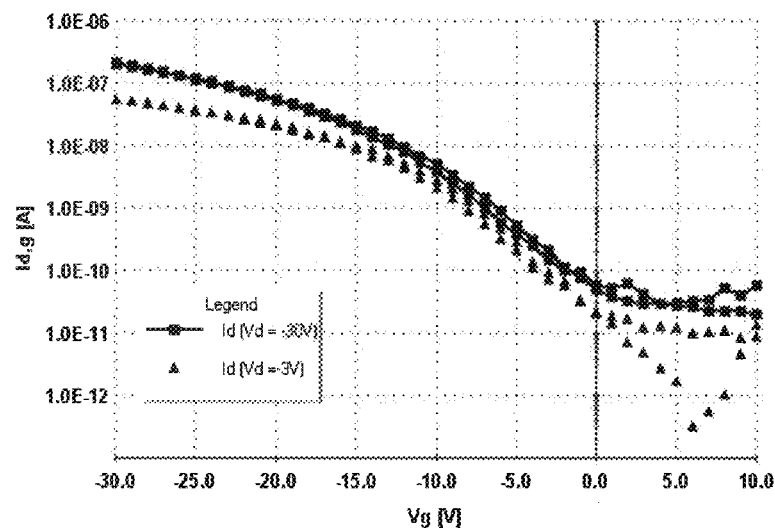
FIG. 5 shows the drain current $I_{ds}$ in relation to the gate voltage $V_{gs}$ (transfer curve) for the top-gate, bottom-contact (TGBC) field effect transistor of example 8 comprising a semiconducting layer formed from Formulation E at a source voltage $V_{ds}$ of −3V (triangle), respectively, −30V (square).
Figure 6:
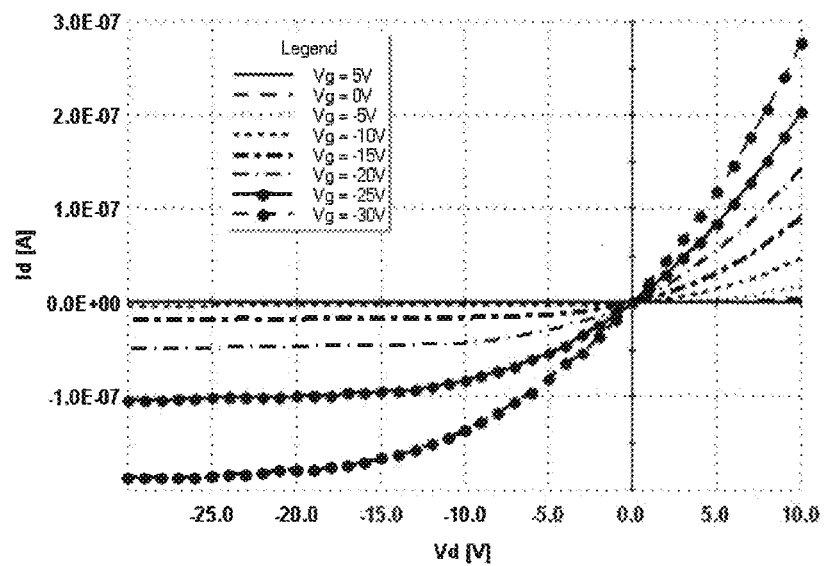
FIG. 6 shows the drain current $I_{ds}$ in relation to the drain voltage $V_{ds}$ (output curve) for the top-gate, bottom-contact (TGBC) field effect transistor of example 8 comprising a semiconducting layer formed from Formulation E at a gate voltage $V_{gs}$ of 5V, 0 V, −5 V, −10 V, −15 V, −20V, −25V and −30 V.

The characteristics of the top gate, bottom contact field effect transistor (FET) device were measured with a Keithley 4200-SCS semiconductor characterization system. The drain current $I_{ds}$ in relation to the gate voltage $V_{gs}$ (transfer curve) for the device comprising a semiconducting layer formed from Formulation E at a source voltage $V_{ds}$ of −3V (triangle), respectively, −30V (square) is shown in FIG. 5. The drain current $I_{ds}$ in relation to the drain voltage $V_{ds}$ (output curve) for polymer device comprising a semiconducting layer formed from Formulation E at a gate voltage $V_{gs}$ of 5V, 0 V, −5 V, −10 V, −15 V, −20V, −25V and −30 V is shown in FIG. 6.

The results are depicted in table 3.

TABLE 3

| semiconducting layer formed from | Mean mobility [cm²/Vs] | Mean $I_{on}/I_{off}$ | Mean $V_{on}$ [V] | Ig [@ 30 V] |
|---|---|---|---|---|
| Formulation E | 0.028 | 4.82E+03 | 2 | 4.47E−10 |

EXAMPLE 9

Photo-Patterning of a Polymer Dielectric Layer Formed from Formulation C on Top of a Polymer Semiconducting Layer A 0.75% by weight solution of the diketopyrrolopyrrole (DPP)-thiophene-polymer of example 1 of WO 2010/049321 in toluene was filtered through a 0.45 micrometer polytetrafluoroethylene (PTFE) filter and applied to a clean silicon dioxide substrate by spin coating (1,500 rpm, 30 seconds). The wet polymer semiconducting layer was dried at 90° C. on a hot plate for 30 seconds. Formulation C, described in example 5, was filtered through a 0.45 micrometer filter and then applied on top of the polymer semiconducting layer by spin coating (3,500 rpm, 30 seconds). The wet polymer dielectric layer was pre-baked at 90° C. for 2 minutes on a hot plate to obtain a 520 nm thick layer. A shadow mask was aligned on top of the dielectric layer before curing using 365 nm (radiation dosage 60 mJ/cm²) with nitrogen flow. The cured film was developed by immersing the film into butyl acetate for 1 minute followed by blowing with nitrogen and heating at 90° C. for 5 minutes.

Figure 7:
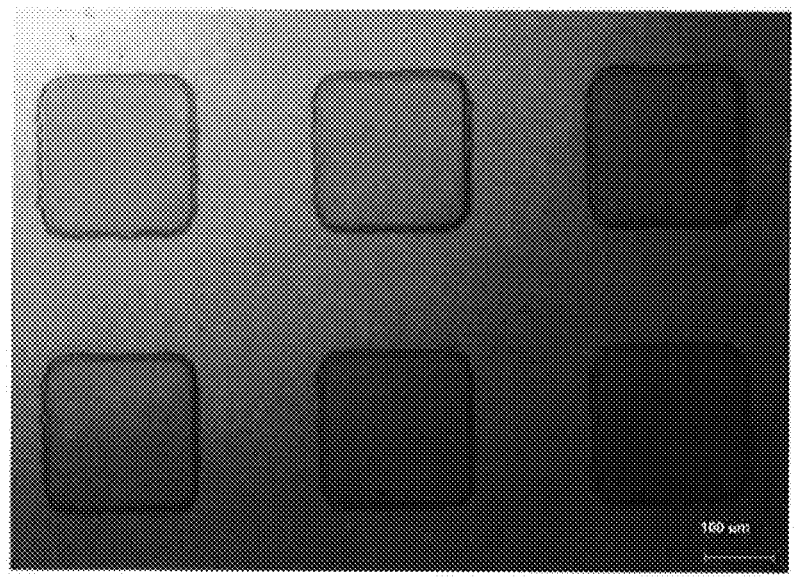
FIG. 7 shows a microscope image of the photo-patterned dielectric layer of example 9 formed from Formulation C taken using an Axio Imager Microscope.

A microscope image of the photo-patterned polymer dielectric layer formed from Formulation C taken using an Axio Imager Microscope is shown in FIG. 7.

EXAMPLE 10

Photo-Patterning of a Semiconductor Layer Formed from Formulation D

Formulation D, described in example 5, was filtered through a 0.45 micrometer filter and then applied on top of the silicon dioxide substrate by spin coating (1,500 rpm, 30 seconds). A shadow mask was aligned on top of the semiconducting layer before curing using 365 nm (radiation dosage 2400 mJ/cm$^2$) at 90° C. The cured film was developed by immersing the film into toluene for 1 minute followed by blowing with nitrogen and heating on a 90° C. hotplate for 5 minutes.

Figure 8:
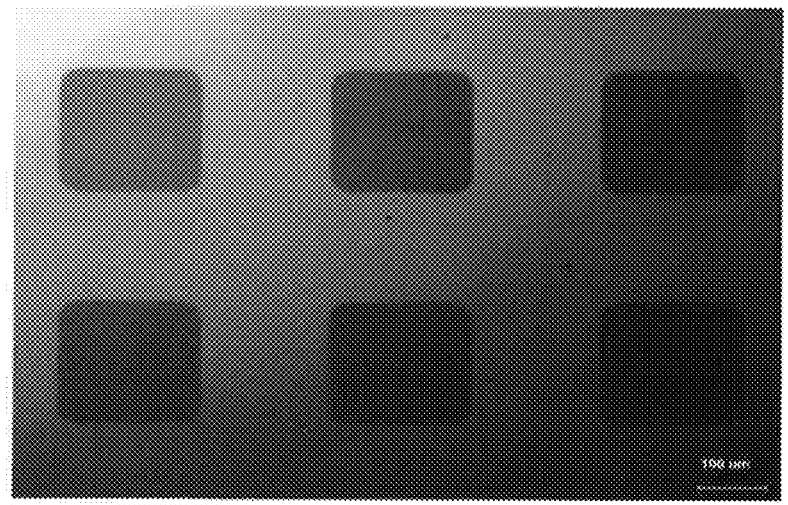
FIG. 8 shows a microscope image of the photo-patterned semiconductor layer of example 10 formed from Formulation D taken using an Axio Imager Microscope.
Figure 9:
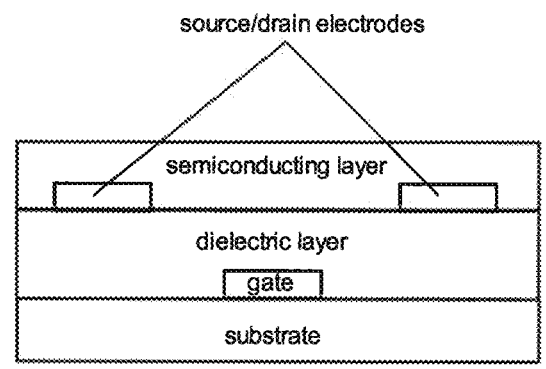
FIG. 9 shows the bottom-gate, bottom-contact design of a field effect transistor (FET) device.
Figure 10:
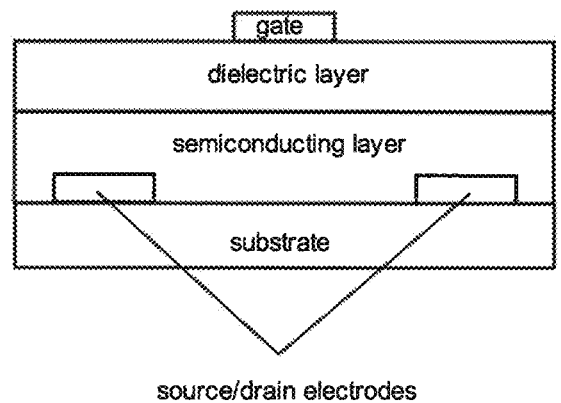
FIG. 10 shows the top-gate, bottom-contact design of a field effect transistor (FET) device.

A microscope image of the photo-patterned semiconductor layer formed from Formulation D taken using an Axio Imager Microscope is shown in FIG. 8.

EXAMPLE 11

Stability of the Cured Dielectric Layer Formed from Formulation A, Respectively, Formulation C Towards Solvent Dissolution Formulation A, respectively, Formulation C, both described in example 5, was filtered through a 0.45 micrometer polytetrafluoroethylene (PTFE) filter and coated on a clean silicon dioxide substrate by spin coating (3500 rpm, 30 s). The wet dielectric layer was heated at 90° C. for 2 minutes on the hotplate to obtain 550 nm thick film. The dielectric layer formed from Formulation A was UV-cured using 365 nm (radiation dosage 960 mJ/cm2) at 90° C. The dielectric layer formed from Formulation C was UV-cured using 365 nm (radiation dosage 1120 mJ/cm2) with nitrogen flow at 100° C. Development of the dielectric layer was done by immersing the dielectric layer into butyl acetate for 1 minute followed by heating at 90° C. for 5 minutes. The thickness of the dielectric layer was measured after curing before development (d1) and after development (d2) using Veeco Dektak 150 to obtain the film retention ratio (d2/d1).

The results are depicted in table 4.

TABLE 4

| | dielectric layer formed from | |
|---|---|---|
| | Formulation A | Formulation C |
| Average Film Retention Ratio [%] | 94 | 99 |

EXAMPLE 12

Stability of the Cured Semiconducting Layer Formed from Formulation D Towards Solvent Dissolution Formulation D described in example 5, was filtered through a 0.45 micrometer polytetrafluoroethylene (PTFE) filter and coated on a clean silicon dioxide substrate by spin coating (1500 rpm, 30 s). The wet polymer semiconducting layer was heated at 90° C. for 2 minutes on the hotplate, cooled to 60° C., and then the polymer semiconducting layer was UV-cured using 365 nm (radiation dosage ca. 2400 mJ/cm$^2$) at 90° C. Development of the polymer semiconducting layer was done by immersing the layer into toluene for 1 minute followed by heating at 90° C. for 5 minutes. The thickness of the polymer semiconducting layer was measured after curing before development (d1) and after development (d2) using Veeco Dektak 150 to obtain the film retention ratio (d2/d1).

The results are depicted in table 5.

TABLE 5

| | semiconducting layer formed from Formulation D |
|---|---|
| Average Film Retention Ratio [%] | 80 |

EXAMPLE 13

Preparation of Capacitor Comprising a Dielectric Layer Formed from Formulation C Formulation C, described in example 5, was filtered through a 0.45 micrometer filter and applied on a clean glass substrate pre-coated with indium tin oxide (ITO) electrodes by spin coating (3500 rpm, 30 seconds). The wet dielectric layer was pre-baked at 90° C. for 2 minutes on a hot plate to obtain a 500 nm thick layer. The dielectric layer was UV-cured using 365 nm (radiation dosage 1120 mJ/cm$^2$) at 100° C. with nitrogen flow. Gold electrodes (area=0.785 mm$^2$) were then vacuum-deposited through a shadow mask on the dielectric layer at <1×10$^{-6}$ Torr (1.3×10$^{-4}$ Pa).

The capacitor thus obtained was characterized in the following way: The relative permittivity was deduced from the complex capacity measured with an Agilent E4980A Precision LCR Meter (signal amplitude 1 V).

The results are depicted in table 6.

TABLE 6

| Frequency | Relative permittivity of capacitor comprising a dielectric layer formed from | |
|---|---|---|
| [Hz] | pure polystyrene | Formulation C |
| 40 | 2.65 | 2.44 |
| 4000 | 2.50 | 2.51 |
| 1000000 | 2.49 | 2.51 |

As can be derived from table 6 the dielectric constant is unaffected by the addition of compound 1d.

EXAMPLE 14

Evaluation of the Effect of the Radiation Dosage on the Cured Polymer Layer

Formulation C, described in example 5, was filtered through a 0.45 micrometer filter and applied on a silicon dioxide substrate by spin coating (3500 rpm, 30 seconds). The wet dielectric layer was pre-baked at 90° C. for 2 minutes on a hot plate to obtain a 550 nm thick layer. The dielectric layer was UV-cured using 365 nm with different radiation dosages using nitrogen flow. Development of the dielectric layer was done by immersing the dielectric layer into butyl acetate for 1 minute followed by heating at 90° C. for 5 minutes. The thickness of the dielectric layer was measured after curing before development (d1) and after development (d2) using Veeco Dektak 150 to obtain the film retention ratio (d2/d1).

Figure 11:
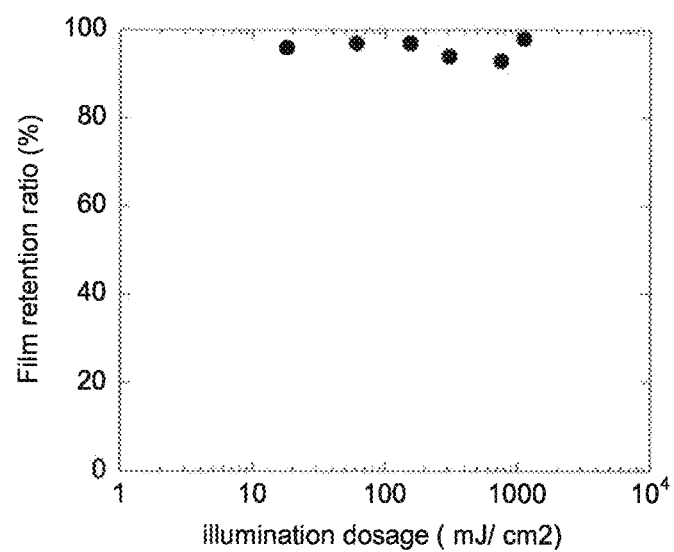
FIG. 11 shows the film retention ratio (d1/d2) in correlation to the applied dosage of radiation for a polymer dielectric layer formed from formulation C.

The film retention ratio (d1/d2) in correlation to the applied dosage of radiation for a dielectric layer formed from formulation C is depicted in FIG. 11.

FIG. 11 shows that the applied radiation dosage can be reduced to 20 mJ/cm$^2$, and the film retention ratio is still retained above 90%.

The invention claimed is:
1. Compounds of formula

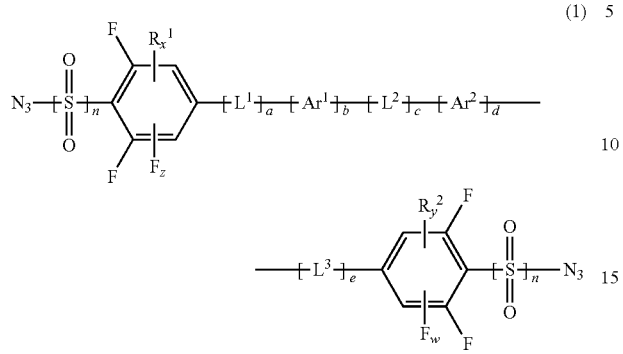
(1)

wherein
a is 0, 1 or 2,
b is 1, 2, 3 or 4,
c is 0 or 1,
d is 0, 1, 2, 3 or 4,
e is 0, 1 or 2,
x is 0, 1 or 2,
y is 0, 1 or 2,
z is 0, 1 or 2,
w is 0, 1 or 2,
n is 0 or 1,
Ar$^1$ and Ar$^2$ are independently from each other and at each occurrence, selected from an aromatic or heteroaromatic moiety, each of which is optionally substituted with one or more substituent R$^a$ selected from the group consisting of C$_{1-20}$-alkyl, C$_{5-8}$-cycloalkyl, C$_{6-14}$-aryl, 5 to 12 membered heteroaryl, COOR$^{10}$, CONR$^{10}$R$^{11}$, COR$^{10}$, SO$_3$R$^{10}$, CN, NO$_2$, halogen, OR$^{10}$, SR$^{10}$, NR$^{10}$R$^{11}$, OCOR$^{10}$ and NR$^{10}$COR$^{11}$,
  wherein R$^{10}$ and R$^{11}$ are independently from each other and at each occurrence, selected from H, C$_{1-20}$-alkyl, C$_{5-8}$-cycloalkyl, C$_{6-14}$-aryl or 5 to 12 membered heteroaryl, and C$_{1-20}$-alkyl and C$_{5-8}$-cycloalkyl are each optionally substituted with one or more substituents R$^{aa}$ at each occurrence, R$^{aa}$ selected from the group consisting of phenyl, COOR$^{12}$, CONR$^{12}$R$^{13}$, COR$^{12}$, SO$_3$R$^{12}$, CN, NO$_2$, halogen, OR$^{12}$, SR$^{12}$, NR$^{11}$R$^{12}$, OCOR$^{12}$ and NR$^{12}$COR$^{13}$, and C$_{6-14}$-aryl and 5 to 12 membered heteroaryl are each optionally substituted with one or more substituent R$^{ab}$ at each occurrence, R$^{ab}$ selected from the group consisting of C$_{1-10}$-alkyl, cyclopentyl, cyclohexyl, COOR$^{12}$, CONR$^{12}$R$^{13}$, COR$^{12}$, SO$_3$R$^{12}$, CN, NO$_2$, halogen, OR$^{12}$, SR$^{12}$, NR$^{12}$R$^{13}$, OCOR$^{12}$ and NR$^{12}$COR$^{13}$, wherein R$^{12}$ and R$^{13}$ are independently from each other and at each occurrence, selected from C$_{1-10}$-alkyl, cyclopentyl, cyclohexyl or phenyl, and
at least two adjacent Ar$^1$, at least two adjacent Ar$^2$, and/or Ar$^1$ and Ar$^2$, both connected to L$^2$ or if c=0 to each other, can be additionally linked by one or more L$^a$,
  wherein L$^a$ is a C$_{1-4}$-alkylene that is optionally substituted with one or more C$_{1-10}$-alkyl, and one or more CH$_2$ groups of C$_{1-4}$-alkylene can be replaced by C═O, (C═O)O, (C═O)NR$^{60}$, SO$_2$—NR$^{60}$, NR$^{60}$, NR$^{60}$R$^{61}$, O or S,
  wherein R$^{60}$ and R$^{61}$ are independently from each other and at each occurrence a C$_{1-10}$-alkyl, L$^1$ and L$^3$ are independently from each other and at each occurrence

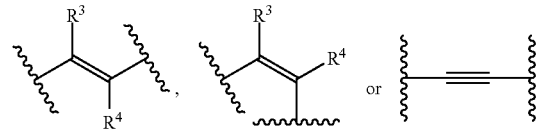

wherein
R$^3$ and R$^4$ are independently from each other and at each occurrence, selected from H, C$_{1-20}$-alkyl, C$_{5-8}$-cycloalkyl, C$_{6-14}$-aryl, 5 to 12 membered heteroaryl, COOR$^{20}$, CONR$^{20}$R$^{21}$, COR$^{20}$, SO$_3$R$^{20}$, CN, NO$_2$, or halogen,
  wherein R$^{20}$ and R$^{21}$ are independently from each other and at each occurrence, selected from H, C$_{1-20}$-alkyl and C$_{5-8}$-cycloalkyl, C$_{6-14}$-aryl or 5 to 12 membered heteroaryl, and C$_{1-20}$-alkyl and C$_{5-8}$-cycloalkyl are each optionally substituted with one or more substituents R$^b$ at each occurrence, R$^b$ selected from the group consisting of phenyl, COOR$^{22}$, CONR$^{22}$R$^{23}$, COR$^{22}$, SO$_3$R$^{22}$, CN, NO$_2$, halogen, OR$^{22}$, SR$^{22}$, NR$^{22}$R$^{23}$, OCOR$^{22}$ and NR$^{22}$COR$^{23}$, and C$_{6-14}$-aryl and 5 to 12 membered heteroaryl are each optionally substituted with one or more substituent R$^c$ at each occurrence, R$^c$ selected from the group consisting of C$_{1-10}$-alkyl, cyclopentyl, cyclohexyl, COOR$^{22}$, CONR$^{22}$R$^{23}$, COR$^{22}$, SO$_3$R$^{22}$, CN, NO$_2$, halogen, OR$^{22}$, SR$^{22}$, NR$^{22}$R$^{23}$, OCOR$^{22}$ and NR$^{22}$COR$^{23}$, wherein R$^{22}$ and R$^{23}$ are independently from each other and at each occurrence, selected from C$_{1-10}$-alkyl, cyclopentyl, cyclohexyl or phenyl,
or, if L$^1$ or L$^3$ are

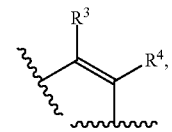

R$^3$ and R$^4$ together with the C-atoms to which they are attached form a 5 to 7-membered non-aromatic ring system A,
L$^2$ is a linking moiety selected from the group consisting of C$_{1-10}$-alkylene, C$_{2-10}$-alkenylene, C$_{5-8}$-cycloalkylene, C$_{1-4}$-alkylene-C$_{5-8}$-cycloalkylene-C$_{1-4}$-alkylene, C$_{1-4}$-alkylene-phenylene-C$_{1-4}$-alkylene, C$_{2-4}$-alkenylene-C$_{5-8}$-cycloalkylene-C$_{2-4}$-alkenylene and C$_{2-4}$-alkenylene-phenylene-C$_{2-4}$-alkenylene, optionally substituted with one or more substituent R$^f$ at each occurrence selected from the group consisting of C$_{1-20}$-alkyl, C$_{5-8}$-cycloalkyl, C$_{6-14}$-aryl, 5 to 12 membered heteroaryl, COOR$^{40}$, CONR$^{40}$R$^{41}$, COR$^{40}$, SO$_3$R$^{40}$, CN, NO$_2$, halogen, OR$^{40}$, SR$^{40}$, NR$^{40}$R$^{41}$, OCOR$^{40}$ and NR$^{40}$COR$^{41}$,
  wherein R$^{40}$ and R$^{41}$ are independently from each other and at each occurrence H, C$_{1-10}$-alkyl, C$_{5-8}$-cycloalkyl, C$_{6-14}$-aryl or 5 to 12 membered heteroaryl, wherein C$_{1-20}$-alkyl and C$_{5-8}$-cycloalkyl are each optionally substituted with one or more substituents R$^{fa}$ at each occurrence, R$^{fa}$ selected from the group consisting of phenyl, COOR$^{42}$, CONR$^{42}$R$^{43}$, COR$^{42}$, $SO_3R^{42}$, CN, $NO_2$, halogen, $OR^{42}$, $SR^{42}NR^{42}R^{43}$, $OCOR^{42}$ and $NR^{42}COR^{43}$, wherein $C_{6-14}$-aryl and 5 to 12 membered heteroaryl are each optionally substituted with one or more substituent $R^{fb}$ at each occurrence, $R^{fa}$ selected from the group consisting of $C_{1-10}$-alkyl, cyclopentyl, cyclohexyl, $COOR^{42}$, $CONR^{42}R^{43}$, $COR^{42}$, $SO_3R^{42}$, CN, $NO_2$, halogen, $OR^{42}$, $NR^{42}R^{43}$, $OCOR^{42}$ and $NR^{42}COR^{43}$, wherein $R^{42}$ and $R^{43}$ are independently from each other and at each occurrence selected from $C_{1-10}$-alkyl, cyclopentyl, cyclohexyl or phenyl, and wherein one or more $CH_2$ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)$NR^{50}$, $SO_2$—$NR^{50}$, $NR^{50}$, $NR^{50}R^{51}$, O or S, wherein $R^{50}$ and $R^{51}$ are independently from each other and at each occurrence $C_{1-10}$-alkyl, and $R^1$ and $R^2$ are independently from each other and at each occurrence, selected from H, $C_{1-20}$-alkyl, $C_{5-8}$-cycloalkyl, $C_{6-14}$-aryl, 5 to 12 membered heteroaryl, $COOR^{30}$, $CONR^{30}R^{31}$, $COR^{30}$, $SO_3R^{30}$, CN, $NO_2$, halogen, $OR^{30}$, $SR^{30}$, $NR^{30}R^{31}$, $OCOR^{30}$ or $NR^{30}COR^{31}$, wherein $R^{30}$ and $R^{31}$ are independently from each other and at each occurrence, selected from H, $C_{1-20}$-alkyl, $C_{5-8}$-cycloalkyl, $C_{6-14}$-aryl or 5 to 12 membered heteroaryl, and $C_{1-20}$-alkyl and $C_{5-8}$-cycloalkyl are each optionally substituted with one or more substituents $R^d$ at each occurrence, $R^d$ selected from the group consisting of phenyl, $COOR^{32}$, $CONR^{32}R^{33}$, $COR^{32}$, $SO_3R^{32}$, CN, $NO_2$, halogen, $OR^{32}$, $SR^{32}$, $NR^{32}N^{33}$, $OCOR^{32}$ and $NR^{32}COR^{33}$, and $C_{6-14}$-aryl and 5 to 12 membered heteroaryl are each optionally substituted with one or more substituent $R^e$ at each occurrence, $R^e$ selected from the group consisting of $C_{1-10}$-alkyl, cyclopentyl, cyclohexyl, $COOR^{32}$, $CONR^{32}R^{33}$, $COR^{32}$, $SO_3R^{32}$, CN, $NO_2$, halogen, $OR^{32}$, $SR^{32}$, $NR^{32}R^{33}$, $OCOR^{32}$ and $NR^{32}COR^{33}$, wherein $R^{32}$ and $R^{33}$ are independently from each other and at each occurrence, selected from $C_{1-10}$-alkyl, cyclopentyl, cyclohexyl or phenyl.

2. Compounds of claim 1, wherein n=0, and the compound of formula (1) is of formula

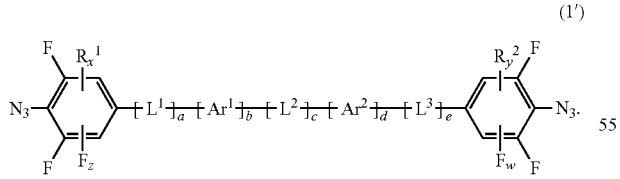

(1')

wherein $R^1$, $R^2$, x, y, z, w, $L^1$, $Ar^1$, $L^2$, $Ar^2$, $L^3$, a, b, c, d and e are as depicted in claim 1.

3. The compounds of claim 1, wherein $Ar^1$ and $Ar^2$ are independently from each other and at each occurrence, selected from an aromatic or heteroaromatic moiety, each of which is optionally substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $NR^{10}R^{11}$, $OCOR^{10}$ and $NR^{10}COR^{11}$, wherein $R^{10}$ and $R^{11}$ are independently from each other and at each occurrence, selected from H, $C_{1-20}$-alkyl, $C_{5-8}$-cycloalkyl, $C_{6-14}$-aryl or 5 to 12 membered heteroaryl, and at least two adjacent $Ar^1$, at least two adjacent $Ar^2$, and/or $Ar^1$ and $Ar^2$, both connected to $L^2$ or if c=0 to each other, can be additionally linked by one or more $L^a$, and $L^1$ and $L^3$ are independently from each other and at each occurrence

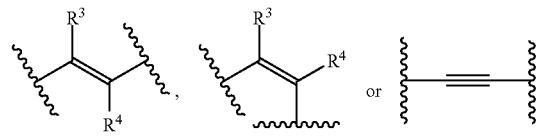

wherein $R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$, or halogen, wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl, or, if $L^1$ or $L^3$ are

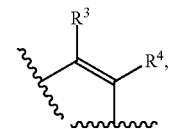

$R^3$ and $R^4$ together with the C-atoms to which they are attached form a 5 to 7-membered non-aromatic ring system A.

4. The compounds of claim 1, wherein $L^2$ is selected from the group consisting of $C_{1-10}$-alkylene, $C_{2-10}$-alkenylene, $C_{5-8}$-cycloalkylene, each of which is optionally substituted with one or more substituent $R^f$ $R^1$ and $R^2$ are independently from each other and at each occurrence H, $C_{1-20}$-alkyl, $C_{6-14}$-aryl, $COOR^{30}$, $CONR^{30}R^{31}$, $COR^{30}$, $SO_3R^{30}$, CN, $NO_2$, halogen, $OR^{30}$, $SR^{30}$, or $NR^{30}R^{31}$, wherein $R^{30}$ and $R^{31}$ are independently from each other and at each occurrence H, $C_{1-20}$-alkyl, $C_{5-8}$-cycloalkyl, $C_{6-14}$-aryl or 5 to 12 membered heteroaryl.

5. The compounds of claim 1, wherein a and e are the same and are 0 or 1, b is 1, 2 or 3, c is 0 or 1, and d is 0, 1, 2 or 3, x and y are the same and are 0, 1 or 2, and z and w are the same and are 0, 1 or 2, $Ar^1$ and $Ar^2$ are independently from each other and at each occurrence a $C_{6-14}$-aromatic or a 5 to 12 membered heteroaromatic moiety, which can be substituted with one or more substituent $R^a$ selected from the group consisting of $C_{1-20}$-alkyl, $C_{5-8}$-cycloalkyl, $C_{6-14}$-aryl, 5 to 12 membered heteroaryl, $COOR^{10}$, $CONR^{10}R^{11}$, $COR^{10}$, $SO_3R^{10}$, CN, $NO_2$, halogen, $OR^{10}$, $SR^{10}$, $NR^{10}R^{11}$, $OCOR^{10}$ and $NR^{10}COR^{11}$, wherein $R^{10}$ and $R^{11}$ are independently from each other and at each occurrence H, $C_{1-20}$-alkyl, $C_{5-8}$-cycloalkyl, $C_{6-14}$-aryl or 5 to 12 membered heteroaryl, wherein at least two adjacent $Ar^1$, at least two adjacent $Ar^2$, and/or $Ar^1$ and $Ar^2$, both connected to $L^2$ or if c=0 to each other, can be additionally linked by one or more $L^a$, wherein $L^a$ is a linking moiety B, $L^1$ and $L^3$ are the same and are

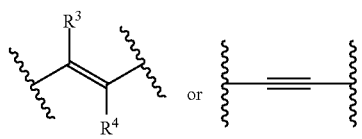 or wherein
$R^3$ and $R^4$ are independently from each other and at each occurrence H, $C_{1-20}$-alkyl, $C_{5-8}$-cycloalkyl, $C_{6-14}$-aryl, 5 to 12 membered heteroaryl, $COOR^{20}$, $CONR^{20}R^{21}$, $COR^{20}$, $SO_3R^{20}$, CN, $NO_2$ or halogen,
wherein $R^{20}$ and $R^{21}$ are independently from each other and at each occurrence H, $C_{1-20}$-alkyl, $C_{5-8}$-cycloalkyl, $C_{6-14}$-aryl or 5 to 12 membered heteroaryl, $L^2$ is a linking moiety A, wherein the linking moiety A is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, which can be substituted with one or more substitutent $R^f$ at each occurrence selected from the group consisting of $C_{1-20}$-alkyl, $C_{5-8}$-cycloalkyl, $C_{6-14}$-aryl, 5 to 12 membered heteroaryl, $COOR^{40}$, $CONR^{40}R^{41}$, $COR^{40}$, $SO_3R^{40}$, CN, $NO_2$, halogen, $OR^{40}$, $NR^{40}R^{41}$, $OCOR^{40}$ and $NR^{40}COR^{41}$,
wherein $R^{40}$ and $R^{41}$ are independently from each other and at each occurrence H, $C_{1-10}$-alkyl, $C_{5-8}$-cycloalkyl, $C_{6-14}$-aryl or 5 to 12 membered heteroaryl, and one or more $CH_2$ groups of $C_{1-10}$-alkylene, $C_{1-4}$-alkylene, $C_{2-10}$-alkenylene, $C_{2-4}$-alkenylene and/or $C_{5-8}$-cycloalkylene can be replaced by C=O, (C=O)O, (C=O)$NR^{50}$, $SO_2$—$NR^{50}$, $NR^{50}$, $NR^{50}R^{51}$, O or S,
wherein $R^{50}$ and $R^{51}$ are independently from each other and at each occurrence $C_{1-10}$-alkyl, and $R^1$ and $R^2$ are the same and are H, $C_{1-20}$-alkyl or $C_{5-8}$-cycloalkyl.

6. The compounds of claim 5, wherein
a and e are the same and are 0 or 1,
b is 1,
c is 0 or 1, and
d is 0 or 1,
x and y are the same and are 0 or 1, and
z and w are the same and are 1 or 2,
$Ar^1$ and $Ar^2$ are the same and are a $C_{6-14}$-aromatic or a 5 to 12 membered heteroaromatic moiety, which can be substituted with one or more substitutent $R^a$ selected from the group consisting of $C_{1-20}$-alkyl and $OR^{10}$, wherein $R^{10}$ is independently from each other and at each occurrence $C_{1-20}$-alkyl, and
wherein $Ar^1$ and $Ar^2$, both connected to $L^2$ or if c=0 to each other, can be additionally linked by one or more $L^a$, wherein $L^a$ is a linking moiety B, wherein the linking moiety B is $C_{1-4}$-alkylene, which can be substituted with one or more $C_{1-10}$-alkyl, $L^1$ and $L^3$ are the same and are

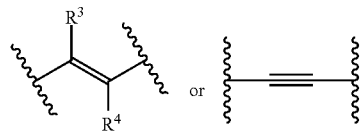 or wherein
$R^3$ and $R^4$ are independently from each other and at each occurrence H, $C_{1-20}$-alkyl, $COOR^{20}$, $CONR^{20}R^{21}$, $COR^{20}$, $SO_3R^{20}$, CN, $NO_2$ or halogen,
wherein $R^{20}$ and $R^{21}$ are independently from each other and at each occurrence H or $C_{1-20}$-alkyl,
$L^2$ is selected from the group consisting of $C_{1-10}$-alkylene, $C_{2-10}$-alkenylene, $C_{5-8}$-cycloalkylene, $C_{1-4}$-alkylene-$C_{5-8}$-cycloalkylene-$C_{1-4}$-alkylene, $C_{1-4}$-alkylene-phenylene-$C_{1-4}$-alkylene, $C_{2-4}$-alkenylene-$C_{5-8}$-cycloalkylene-$C_{2-4}$-alkenylene and $C_{2-4}$-alkenylene-phenylene-$C_{2-4}$-alkenylene, wherein one or more $CH_2$ groups of $C_{1-10}$alkylene, $C_{1-4}$-alkylene, $C_{2-10}$-alkenylene, $C_{2-4}$-alkenylene acid/or $C_{5-8}$-cycloalkylene can be replaced by C=O, (C=O)O, (C=O)$NR^{50}$, $SO_2$—$NR^{50}$, $NR^{50}$, $NR^{50}R^{51}$, O or S,
wherein $R^{50}$ and $R^{51}$ are independently from each other and at each occurrence $C_{1-10}$-alkyl, and
$R^1$ and $R^2$ are the same and are branched $C_{3-6}$-alkyl.

7. The compounds of claim 6, wherein
x and y are the same and are 0,
z and w are the same and are 2,
$Ar^1$ and $Ar^2$ are the same and are

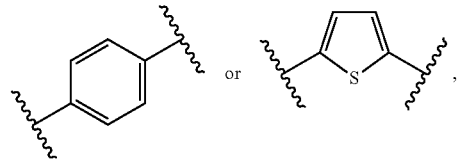 [SMILES: *c1ccc(*)cc1 ; *c1ccc(*)s1] or , which can be substituted with one or more substitutent $R^a$ selected from the group consisting of $C_{1-10}$-alkyl and $OR^{10}$,
wherein $R^{10}$ is independently from each other and at each occurrence $C_{1-10}$-alkyl, and
wherein $Ar^1$ and $Ar^2$, both connected to $L^2$ or if c=0 to each other, can be additionally linked by one or more $L^a$, wherein $L^a$ is a linking moiety B, wherein the linking moiety B is methylene substituted with one or more $C_{1-10}$-alkyl,
$L^1$ and $L^3$ are the same and are

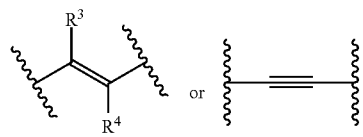 or wherein
$R^3$ and $R^4$ are H, and
$L^2$ is $C_{1-10}$-alkylene, wherein one or more $CH_2$ groups of $C_{1-10}$-alkylene can be replaced by C=O, (C=O)O, (C=O)$NR^{50}$, $SO_2$—$NR^{50}$, $NR^{50}$, $NR^{50}R^{51}$, O or S, wherein $R^{50}$ and $R^{51}$ are independently from each other and at each occurrence $C_{1-10}$-alkyl.

8. A process for the preparation of the compounds of formula

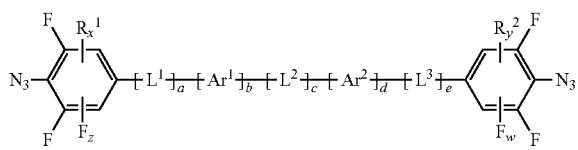

(1)

of claim 1,
which process comprises the step of reacting a compound of formula

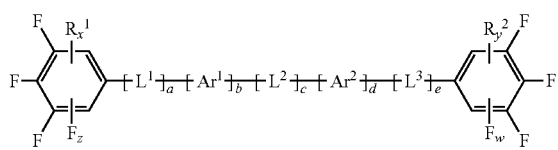

(2)

wherein a, b, c, d, e, x, y, z, w, $Ar^1$, $Ar^2$, $L^1$, $L^3$, $L^2$, $R^1$ and $R^2$ are as depicted for the compound of formula (1), with $M^{m+}(N_3^-)_m$,
wherein m is 1, 2 or 3, and M is a metal.

9. A solution comprising one or more compounds of formula (1) of claim 1, one or more polymers and one or more solvents.

10. The solution of claim 9, wherein the one or more polymers are dielectric polymers.

11. The solution of claim 10, wherein the one or more polymers are styrene-based polymers.

12. A process for the preparation of a device which process comprises the steps of
(i) depositing the solution of claim 9 on a support in order to form a layer, and
(ii) exposing the layer of step (i) to radiation in order to form a polymer layer.

13. The process of claim 12, wherein the device is an electronic device.

14. The process of claim 13, wherein the radiation of step (ii) has a wavelength in the range of 300 to 450 nm.

15. A device obtainable by the process of claim 12.

16. A polymer prepared with a compound of claim 1 as a cross-linker.

17. The compounds of claim 2, wherein
$R^1$ and $R^2$ are independently from each other and at each occurrence H, $C_{1-20}$-alkyl, $C_{5-8}$-cycloalkyl, $C_{6-14}$-aryl, 5 to 12 membered heteroaryl, $COOR^{30}$, $CONR^{30}R^{31}$, $COR^{30}$, $SO_3R^{30}$, CN, $NO_2$, halogen, $OR^{30}$, $SR^{30}$, $NR^{30}R^{31}$, $OCOR^{30}$ or $NR^{30}COR^{31}$,
wherein $R^{30}$ and $R^{31}$ are independently from each other and at each occurrence H, $C_{1-20}$-alkyl, $C_{5-8}$-cycloalkyl, $C_{6-14}$-aryl or 5 to 12 membered heteroaryl.

* * * * *